United States Patent
Tomita et al.

(10) Patent No.: US 8,927,493 B2
(45) Date of Patent: Jan. 6, 2015

(54) PROMOTER FOR REGENERATION OF TENDON-BONE JUNCTION TISSUE OR LIGAMENT-BONE JUNCTION TISSUE

(75) Inventors: Katsuro Tomita, Kanazawa (JP); Hiroyuki Tsuchiya, Kanazawa (JP); Katsuhiko Kitaoka, Kanaszawa (JP); Junsuke Nakase, Kanazawa (JP); Keigo Hanada, Toyonaka (JP); Kunio Matsumoto, Kanazawa (JP)

(73) Assignee: Kringle Pharma, Inc., Toyonaka-Shi, Osaka (JP)

( * ) Notice: Subject to any disclaimer, the term of this patent is extended or adjusted under 35 U.S.C. 154(b) by 379 days.

(21) Appl. No.: 13/123,091

(22) PCT Filed: Oct. 8, 2009

(86) PCT No.: PCT/JP2009/067570
§ 371 (c)(1),
(2), (4) Date: Apr. 7, 2011

(87) PCT Pub. No.: WO2010/041716
PCT Pub. Date: Apr. 15, 2010

(65) Prior Publication Data
US 2011/0312887 A1     Dec. 22, 2011

(30) Foreign Application Priority Data
Oct. 10, 2008   (WO) ................ PCT/JP2008/068507

(51) Int. Cl.
*A61K 38/18*     (2006.01)
(Continued)

(52) U.S. Cl.
CPC ............. *A61K 38/1833* (2013.01); *A61K 48/00* (2010.01); *C07K 14/4753* (2013.01)
USPC ......... 514/9.5; 514/16.5; 514/16.7; 514/17.1; 530/399

(58) Field of Classification Search
None
See application file for complete search history.

(56) References Cited

U.S. PATENT DOCUMENTS 6,699,837 B2 *   3/2004   Nakamura ................... 514/7.6
2003/0153849 A1   8/2003   Huckle et al.
(Continued)

FOREIGN PATENT DOCUMENTS

| EP | 0 461 560 A1 | 6/1991 |
| JP | 2777678 B2 | 7/1998 |

(Continued)

OTHER PUBLICATIONS

Tolbert et al., PNAS, 2010, vol. 107(30):13264-13269.*

(Continued)

*Primary Examiner* — Xiaozhen Xie
(74) *Attorney, Agent, or Firm* — Katz, Quintos & Hanson, LLP

(57) ABSTRACT

An object of the present invention is to provide a drug for promoting the regeneration of tendon-bone junction tissue or ligament-bone junction tissue. The present invention relates to a promoter for regeneration of tendon-bone junction tissue or ligament-bone junction tissue including the following (1) or (2) as an active ingredient:
  (1) the following (1-a), (1-b), or (1-c)
    (1-a) HGF protein,
    (1-b) a partial peptide of HGF protein, the peptide having an effect of promoting regeneration of tendon-bone junction tissue or ligament-bone junction tissue,
    (1-c) a salt of (1-a) or (1-b);
  (2) DNA including the following (2-a), (2-b), or (2-c),
    (2-a) DNA encoding HGF protein,
    (2-b) DNA encoding a partial peptide of HGF protein, the peptide having an effect of promoting regeneration of tendon-bone junction tissue or ligament-bone junction tissue,
    (2-c) DNA encoding a protein or a peptide, the protein or the peptide having an effect of promoting regeneration of tendon-bone junction tissue or ligament-bone junction tissue, and the DNA hybridizing with DNA comprising a base sequence complementary to (2-a) or (2-b) under a stringent condition.

5 Claims, 2 Drawing Sheets
(1 of 2 Drawing Sheet(s) Filed in Color)

(51) Int. Cl.
C07K 14/475 (2006.01)
A61P 19/00 (2006.01)
A61P 19/04 (2006.01)
A61K 48/00 (2006.01)

(56) References Cited

U.S. PATENT DOCUMENTS

2004/0078077 A1* 4/2004 Binette et al. .............. 623/13.17
2010/0081617 A1 4/2010 Okano et al.

FOREIGN PATENT DOCUMENTS

| JP | 11-1499 | | 1/1999 |
|---|---|---|---|
| WO | WO 01/66130 | * | 9/2001 |
| WO | WO 2008/105507 A1 | | 9/2008 |

OTHER PUBLICATIONS

Dapeng Jiang, et al.; "Suppression of the production of extracellular matrix and α-smooth muscle actin induced by transforming growth factor-β1 in fibroblasts of the flexor tendon sheath by hepatocyte growth factor"; *Scand J Plast Reconstr Surg Hand Surg*; vol. 42; No. 4; 2008; pp. 169-173.
Supplementary European Search Report dated Feb. 27, 2012, in counterpart European Application No. EP 09819250.
T. Nakamura, et al.; Partial Purification and Charaterization of Hepatocyte Growth Factor from Serum of Hepatectomized Parts; *Biochemical and Biophysical Research Communications*; vol. 122; No. 3; Aug. 16, 1984; pp. 1450-1459 (10 Sheets).
M. Sanchez, et al.; "Comparison of Surgically Repaired Achilles Tendon Tears Using Platelet-Rich Fibrin Matrices;" The American Journal of Sports Medicine; vol. 35; No. 2; 2007; pp. 245-251 (7 Sheets)/International Search Report.
T. Natsuume, et al.; "Initial Effect of HGF Gene Transfection on Tendon Repair: Examination of Rat Model with Patellar Tendon Injury;" vol. 72; No. 8; 1998; p. S1254, cover sheet and translation (5 Sheets)/International Search Report/p. 3 of specification, Journal of Japanese Orthopaedic Association.
S. Yamazaki, et al.; The Effect of Transforming Growth Factor -beta-1 on Intraosseous Healing of Flexor Tendon Autograft Replacement of Anterior Cruciate Ligament in Dogs; Arthroscopy: The Journal of Arthroscopic and Related Surgery; vol. 21; No. 9; 2005; pp. 1034-1041 (8 Sheets)/International Search Report/p. 3 of specification.
C.B. MA, et al.; "Bone Morphogenic Proteins-Signaling Plays a Role in Tendon-to-Bone Healing;" The American Journal of Shorts Medicine; vol. 35; No. 4; pp. 597-604 (8 Sheets)/International Search Report/International Search Report, (2007).
C. Hsu, et al.; "Clinical Implications of Growth Factors in Flexor Tendon Wound Healing;" The Journal of Hand Surgery; vol. 29; 2004; pp. 551-563 (13 Sheets)/International Search Report.
T.W. Lin, et al.; "Biomechanics of tendon injury and repair;" Journal of Biomechanics; vol. 37; 2004; pp. 865-877 (13 Sheets)/International Search Report.
D. Jiang, et al.; HGF suppresses the production of collagen type III and alpha-SMA induced by TGF-beta-1 in healing fibroblasts; Eur. J. Appl. Physiol.; vol. 103; 2008; pp. 489-493 and endsheet (6 Sheets)/International Search Report.
S.A. Rodeo, et al.; "Tendon-Healing in a Bone Tunnel;" The Journal of Bone and Joint Surgery, Incorporated; vol. 75-A; No. 12; Dec. 1993; 1795-1803 (9 Sheets)/p. 3 of specification.
S.A. Rodeo, et al.; "Use of Recombinant Human Bone Morphogenic Protein-2 to Enhance Tendon Healing in a Bone Tunnel;" The American Journal of Sports Medicine; vol. 27; No. 4; 1999; pp. 476-488 (13 Sheets)/p. 3 of specification.
T. Nakamura, et al.; "Partial Purification and Characterization of Hepatocyte Growth Factor From Serum of Hepatectomized Rats;" Biochemical and Biophysical Research Communications; vol. 122; No. 3; Aug. 16, 1984; pp. 1450-1458 (9 Sheets)/p. 3 of specification.

T. Nakamura, et al.; "Molecular cloning and expression of human hepatocyte growth factor;" Nature; vol. 342; Nov. 23, 1989; pp. 440-443 (4 Sheets)/p. 3 of specification.
K. Matsumoto, et al.; "Hepatocyte Growth Factor (HGF) as a Tissue Organizer for Organogenesis and Regeneration;" Biochemical and Biophysical Research Communications; vol. 239; 1997; pp. 639-644 (6 Sheets)/p. 3 of specification.
International Search Report for International Application No. PCT/JP2009/067570 dated Dec. 14, 2009.
Miyazawa, Keiji, et al.; "Molecular Cloning and Sequence Analysis of cDNA for Human Hepatocyte Growth Factor," Biochemical and Biophysical Research Communications, vol. 163, No. 2 (1989), pp. 967-973.
UniProtKB/Swiss-Prot: P14210.2, May 29, 2013, "RecName: Full=Hepatocyte growth factor; AltName: Full=Hepatopoietin-A; AltName: Full=Scatter factor; Short=SF; Contains: RecName: Full—Hepatocyte growth factor alpha chain; Contains: RecName: Full=Hepatocyte growth factor beta chain; Flags: Precursor".
NCBI Reference Sequence: NP_001010932.1, Jul. 7, 2013, "hepatocyte growth factor isoform 3 precursor [*Homo sapiens*]".
GenBank: BAA14348.1, Aug. 2, 2007, "hepatocyte growth factor [*Homo sapiens*]".
GenBank: AAC71655.1, Dec. 10, 2008, "hepatocyte growth factor [*Homo sapiens*]".
Fukuta, Kazuhiro, et al., "Multiple biological responses are induced by glycosylation-deficient hepatocyte growth factor," Biochem. J., vol. 388 (2005), pp. 555-562.
GenBank: AAB31855.1, Jan. 24, 1995, "hepatocyte growth factor [*Mus* sp.]".
NCBI Reference Sequence: NP_034557.3, Jul. 15, 2013, "hepatocyte growth factor precursor [*Mus musculus*]".
GenBank: BAA01065.1, Dec. 27, 2006, "hepatocyte growth factor precursor [*Mus musculus*]".
GenBank: BAA01064.1, Dec. 27, 2006, "hepatocyte growth factor precursor [*Mus musculus*]".
NCBI Reference Sequence: NP_058713.1, Apr. 14, 2013, hepatocyte growth factor preproprotein [*Rattus norvegicus*].
NCBI Reference Sequence: NP_001026921.1, Apr. 18, 2013, hepatocyte growth factor precursor [*Bos taurus*].
GenBank: BAD02475.1, Aug. 25, 2006, "hepatocyte growth factor [*Bos taurus*]".
NCBI Reference Sequence: NP_001009830.1, Apr. 18, 2013, "hepatocyte growth factor precursor [*Felis catus*]".
GenBank: BAC10545.1, Aug. 18, 2007, "hepatocyte growth factor [*Felis catus*]".
GenBank: BAB21499.1, Jan. 27, 2001, "hepatocyte growth factor HGF [*Felis catus*]".
NCBI Reference Sequence NP_001002964.1, Apr. 18, 2013, "hepatocyte growth factor precursor [*Canis lupus miliaris*]".
GenBank: BAC57560.1, Feb. 27, 2009, "hepatocyte growth factor [*Canis lupus familiaris*]".
NCBI Reference Sequence: XP_519174.2, Oct. 25, 2012, "Predicted: hepatocyte growth factor isoform 2 [*Pan troglodytes*]".
Weidner, K. Michael, et al., "Evidence for the identity of human scatter factor and human hepatocyte growth factor," Proc. Natl. Acad. Sci. USA, vol. 88 (1991), pp. 7001-7005.
GenBank: M73240.1, Mar. 24, 1995, "Human (clone SF2) hepatocyte growth factor (HGF) mRNA, complete cds".
GenBank: AC004960.1, Dec. 10, 2008, "*Homo sapiens* Pac clone RP5-1098B1 from 7q11.23-q21, complete sequence".
GenBank: AY246560.1, Mar. 12, 2003, "*Homo sapiens* hepatocyte growth factor (hepapoietin A; scatter factor) (HGF) gene, complete cds".
GenBank: M29145.1, Nov. 8, 1994, "Human hepatocyte growth factor (hHGF) mRNA, complete cds".
GenBank: 571816.1, Jan. 24, 1995, "hepatocyte growth factor [mice, liver, mRNA Partial, 2281 nt]".
NCBI Reference Sequence: NM_010427.4, Jul. 15, 2013, "*Mus musculus* hepatocyte growth factor (Hgf), mRNA".
GenBank: D10213.1, Dec. 27, 2006, "*Mus musculus* mRNA for hepatocyte growth factor, complete cds".
GenBank: D10212.1, Dec. 27, 2006, "*Mus musculus* mRNA for hepatocyte growth factor, complete cds".

(56) References Cited

OTHER PUBLICATIONS

NCBI Reference Sequence: NM_017017.2, Apr. 14, 2013, "*Rattus norvegicus* hepatocyte growth factor (Hgf), mRNA".

NCBI Reference Sequence: NM_001031751.1, Apr. 18, 2013, "*Bos taurus* hepatocyte growth factor (hepapoietin A; scatter factor) (HGF), mRNA".

GenBank: AB110822.1, Aug. 25, 2006, "*Bos taurus* hgf mRNA for hepatocyte growth factor, complete cds".

NCBI Reference Sequence NM_1009830.1, Apr. 18, 2013, "*Felis catus* hepatocyte growth factor (hepapoietin A; scatter factor) (HGF), mRNA".

GenBank: AB080187.1, Aug. 18, 2007, "*Felis catus* HGF mRNA for hepatocyte growth factor, complete cds".

GenBank: AB046610.1, Jan. 27, 2001, "*Felis catus* mRNA for hepatocyte growth factor HGF, complete cds".

NCBI Reference Sequence NM_001002964.1, Apr. 18, 2013, "*Canis lupus familiaris* hepatocyte growth factor (hepapoietin A; scatter factor) (HGF), mRNA".

GenBank: AB090353.1, Feb. 27, 2009, "*Canis lupus familiaris* HGF mRNA for hepatocyte growth factor, complete cds".

NCBI Reference Sequence: XM_519174.4, Oct. 25, 2012, "Predicted: Pan troglodytes hepatocyte growth factor (hepapoietin A; scatter factor), transcript variant 2 (HGF), mRNA".

GenBank: M60718.1, Nov. 8, 1994, "Human hepatocyte growth factor mRNA, complete cds".

* cited by examiner

PROMOTER FOR REGENERATION OF TENDON-BONE JUNCTION TISSUE OR LIGAMENT-BONE JUNCTION TISSUE

TECHNICAL FIELD

The present invention relates to a promoter for the regeneration of tendon-bone junction tissue or ligament-bone junction tissue.

BACKGROUND ART

Recently, injuries such as tendon or ligament ruptures in sports, traffic accidents, etc., are increasing. In regard to ligaments, since the anterior cruciate ligament (ACL) and the posterior cruciate ligament (PCL) are tissues that connect the femur to the tibia through a knee joint, when the ACL or PCL is ruptured, the stability of the knee joint cannot be maintained. Once ruptured, ligaments cannot be oversewn; therefore, in many cases, ligament reconstructive surgery is utilized to repair or replace injured ligaments.

For example, in ACL reconstructive surgery in which a damaged ACL is reconstructed by replacing it with a ligament graft, the patellar tendon with bone blocks is conventionally utilized as a graft. Such ACL reconstructive surgery allows rehabilitation to start early because the patellar tendon can function as a ligament when the bones attach to each other. However, the surgery also has disadvantages such as postoperative pain and muscle weakness.

In recent years, ACL reconstructive surgery that utilizes as a tendon graft, a hamstring tendon (knee flexor tendon, semitendinosus tendon, gracilis tendon), which is one of the muscle tendons used in bending the knees has been reported (for example, see Non Patent Literature 1). More specifically, the surgery includes the steps of forming a bone tunnel (hole) in the upper end of the tibia and the lower end of the femur, placing one end of the tendon graft in the femur side of the bone tunnel, and placing the other end of the tendon graft in the tibia side of the bone tunnel. Thus, the tendon graft runs between the femur and the tibia, and thereby functions. The tendon graft performs substantially the same function as the original ACL, thereby allowing the recovery of normal function in the knee joints. However, since the object of ACL reconstructive surgery is to reconstruct the normal ACL function and the kinematics of the knee joints, it is necessary to reconstruct the tendon-bone joint tissue in the part where the tendon graft comes in contact with the bone surface in the bone tunnel with enough strength.

For this reason, ACL reconstructive surgery has a disadvantage such that a long period of time is required before the tendon graft can function as a ligament.

As a drug for promoting the regeneration of tendon-bone junction tissue, BMP-2 (Bone Morphogenetic Protein-2: Non-Patent Literature 2), TGF-β1 (Transforming Growth Factor-β1: Non-Patent Literature 3), etc., are known; however, they have not yet been used in practice as a drug for promoting the regeneration of tendon-bone junction tissue.

HGF (Hepatocyte Growth Factor, hereinafter referred to as "HGF protein") was first identified as a potent mitogen for mature hepatocytes, and was determined by DNA cloning in 1989 (Non-Patent Literatures 4 and 5). Thereafter, HGF has been reported as having various effects such as angiogenesis, cell differentiation, cell proliferation, anti-apoptosis, etc., in various tissues. As to its effect in tendon tissue, it is reported that when HGF gene plasmid DNA is introduced into a wound made in the center of rat patellar tendon, the orientation of the developing collagen fibers in the wound is improved (Non-Patent Literature 6). However, tendon-bone junction tissue has a structure different from the tendon itself, and is a complicated tissue to adhere (fixate or fuse) a bone and a tendon, which are completely different from each other histologically. Non-Patent Literature 6 does not disclose or suggest the regeneration of such complicated tendon-bone junction tissue. Further, HGF protein is reported to inhibit the expression of TGF-β1, which, as mentioned previously, is known as a drug that promotes the regeneration of tendon-bone junction tissue (Non Patent Literature 7).

CITATION LIST

Non-Patent Literatures

NPL 1: S. A. Rodeo et al., The Journal of Bone and Joint Surgery; JBJS, 1993, Vol. 75-A, Issue 12, pp. 1795-1803.
NPL 2: S. A. Rodeo et al., The American Journal of Sports Medicine, 1999, Vol. 27, pp. 476-488
NPL 3: Shuji Yamazaki et al., The Journal of Arthroscopic and Related Surgery; JBJS, 2005, Vol. 21, Issue 9, pp. 1034-1041
NPL 4: Toshikazu Nakamura et al., Biochemical and Biophysical Research Communications, 1984, Vol. 122, pp. 1450-1459
NPL 5: Toshikazu Nakamura et al., Nature, 1989, Vol. 342, pp. 440-443
NPL 6: Takashi Natsu-ume et al., Journal of the Japanese Orthopaedic Association, 1998, Vol. 72, Issue 8, 51254
NPL 7: Kunio Matsumoto and Toshikazu Nakamura, Biochemical and Biophysical Research Communications, 1997, Vol. 239, pp. 639-644

SUMMARY OF INVENTION

Technical Problem

An object of the present invention is to provide a drug for promoting the regeneration of tendon-bone junction tissue or ligament-bone junction tissue. Particularly, an object of the present invention is to provide a drug for promoting the regeneration of tendon-bone junction tissue or ligament-bone junction tissue at a contact site between a bone and a tendon or ligament graft after ACL reconstructive surgery etc., or in a space between a bone and a tendon or ligament graft after ACL reconstructive surgery etc.

Solution to Problem

The present inventors conducted extensive research to solve the above problems. Consequently, they found that HGF protein has an effect of promoting the regeneration of tendon-bone junction tissue or ligament-bone junction tissue, and accomplished the invention.

Specifically, the present invention relates to a promoter for the regeneration of tendon-bone junction tissue or ligament-bone junction tissue.

1. A promoter for regeneration of tendon-bone junction tissue or ligament-bone junction tissue, comprising the following (1) or (2) as an active ingredient:
   (1) the following (1-a), (1-b), or (1-c)
   (1-a) HGF (Hepatocyte Growth Factor) protein,
   (1-b) a partial peptide of HGF protein, the peptide having an effect of promoting regeneration of tendon-bone junction tissue or ligament-bone junction tissue,
   (1-c) a salt of (1-a) or (1-b);

(2) DNA comprising the following (2-a), (2-b), or (2-c),
(2-a) DNA encoding HGF protein,
(2-b) DNA encoding a partial peptide of HGF protein, the peptide having an effect of promoting regeneration of tendon-bone junction tissue or ligament-bone junction tissue,
(2-c) DNA encoding a protein or a peptide, the protein or the peptide having an effect of promoting regeneration of tendon-bone junction tissue or ligament-bone junction tissue, and the DNA hybridizing with DNA comprising a base sequence complementary to (2-a) or (2-b) under a stringent condition.

2. The promoter according to Item 1, wherein the active ingredient is the following (1-a), (1-b), or (1-c):
(1-a) HGF protein,
(1-b) a partial peptide of HGF protein, the peptide having an effect of promoting regeneration of tendon-bone junction tissue or ligament-bone junction tissue,
(1-c) a salt of (1-a) or (1-b).

3. The promoter according to Item 1 or 2, wherein the HGF protein is the following (1-d) or (1-e):
(1-d) a protein having an amino acid sequence represented by SEQ ID NO: 3 or 4,
(1-e) a protein having an amino acid sequence that is substantially equal to an amino acid sequence represented by SEQ ID NO: 3 or 4, and having an effect of promoting regeneration of tendon-bone junction tissue or ligament-bone junction tissue.

Herein, an example of protein (1-e) includes "a protein that has an amino acid sequence at least 85% homologous to an amino acid sequence represented by SEQ ID NO: 3 or 4, and has an effect of promoting the regeneration of tendon-bone junction tissue or ligament-bone junction tissue".

4. The promoter according to Item 1, wherein the active ingredient is DNA comprising the following (2-a), (2-b), or (2-c):
(2-a) DNA encoding HGF protein,
(2-b) DNA encoding a partial peptide of HGF protein, the peptide having an effect of promoting regeneration of tendon-bone junction tissue or ligament-bone junction tissue,
(2-c) DNA encoding a protein or a peptide, the protein or the peptide having an effect of promoting regeneration of tendon-bone junction tissue or ligament-bone junction tissue, and the DNA hybridizing with DNA comprising a base sequence complementary to (2-a) or (2-b) under a stringent condition.

5. The promoter according to Item 1 or 4, wherein the DNA encoding HGF protein is the following (2-d) or (2-e):
(2-d) DNA having a base sequence represented by SEQ ID NO: 1 or 2,
(2-e) DNA that encodes a protein having an effect of promoting regeneration of tendon-bone junction tissue or ligament-bone junction tissue, and that hybridizes with DNA having a base sequence complementary to the base sequence represented by SEQ ID NO: 1 or 2 under a stringent condition.

6. The promoter according to any one of Items 1, 4, and 5, wherein the DNA is inserted into a herpes simplex virus type 1 (HSV-1) vector, a Sendai virus envelope (HVJ-E) vector, an adenovirus vector, or an adeno-associated virus vector.

7. The promoter according to any one of Items 1 to 6, which is in a form of topical application.

Further, the present invention relates to a use of HGF protein, or DNA encoding HGF protein.

8. Use of the following (1) or (2) for manufacturing a promoter for regeneration of tendon-bone junction tissue or ligament-bone junction tissue:
(1) the following (1-a), (1-b), or (1-c),
(1-a) HGF protein,
(1-b) a partial peptide of HGF protein, the peptide having an effect of promoting regeneration of tendon-bone junction tissue or ligament-bone junction tissue,
(1-c) a salt of (1-a) or (1-b),
(2) DNA comprising the following (2-a), (2-h), or (2-c),
(2-a) DNA encoding HGF protein,
(2-b) DNA encoding a partial peptide of HGF protein, the peptide having an effect of promoting regeneration of tendon-bone junction tissue or ligament-bone junction tissue,
(2-c) DNA encoding a protein or a peptide, the protein or the peptide having an effect of promoting regeneration of tendon-bone junction tissue or ligament-bone junction tissue, and the DNA hybridizing with DNA comprising a base sequence complementary to (2-a) or (2-b) under a stringent condition.

9. The following (1) or (2) for use in a method of promoting regeneration of tendon-bone junction tissue or ligament-bone junction tissue:
(1) the following (1-a), (1-b), or (1-c),
(1-a) HGF protein,
(1-b) a partial peptide of HGF protein, the peptide having an effect of promoting regeneration of tendon-bone junction tissue or ligament-bone junction tissue,
(1-c) a salt of (1-a) or (1-b),
(2) DNA comprising the following (2-a), (2-b), or (2-c),
(2-a) DNA encoding HGF protein,
(2-b) DNA encoding a partial peptide of HGF protein, the peptide having an effect of promoting regeneration of tendon-bone junction tissue or ligament-bone junction tissue,
(2-c) DNA encoding a protein or a peptide, the protein or the peptide having an effect of promoting regeneration of tendon-bone junction tissue or ligament-bone junction tissue, and the DNA hybridizing with DNA comprising a base sequence complementary to (2-a) or (2-b) under a stringent condition.

10. A method for promoting regeneration of tendon-bone junction tissue or ligament-bone junction tissue comprising: administering the following (1) or (2) to a patient with tendon-bone junction tissue injury or ligament-bone junction tissue injury:
(1) the following (1-a), (1-b), or (1-c),
(1-a) HGF protein,
(1-b) a partial peptide of HGF protein, the peptide having an effect of promoting regeneration of tendon-bone junction tissue or ligament-bone junction tissue,
(1-c) a salt of (1-a) or (1-b),
(2) DNA comprising the following (2-a), (2-b), or (2-c),
(2-a) DNA encoding HGF protein,
(2-b) DNA encoding a partial peptide of HGF protein, the peptide having an effect of promoting regeneration of tendon-bone junction tissue or ligament-bone junction tissue,
(2-c) DNA encoding a protein or a peptide, the protein or the peptide having an effect of promoting regeneration of tendon-bone junction tissue or ligament-bone junction tissue, and the DNA hybridizing with DNA comprising a base sequence complementary to (2-a) or (2-b) under a stringent condition.

Advantageous Effects of Invention

The promoter for the regeneration of tendon-bone junction tissue or ligament-bone junction tissue of the present invention can enhance the regeneration of the tendon-bone junction tissue or the ligament-bone junction tissue at a site in which a bone is in contact with a ligament or tendon graft separated from the bone, or in a space between the bone and the ligament or tendon graft. Thus, the present invention can promote adhesion (fixation or fusion) between a bone and a tendon or ligament that is separated from the bone by injury, rupture, etc.

Further, since the present invention can enhance the regeneration of tendon-bone junction tissue or ligament-bone junction tissue in ligament reconstructive surgery of limb joints (e.g., knee, ankle, elbow, and shoulder) including ACL reconstructive surgery, PCL reconstructive surgery, collateral ligament reconstructive surgery, MPFL (medial patellofemoral ligament) reconstructive surgery, ankle lateral ligament reconstructive surgery, ulnar ligament reconstructive surgery, and tendon repair surgery etc., adhesion (fixation or fusion) between a bone and a tendon or ligament graft can be enhanced.

Therefore, the present invention results in a faster recovery of patients after ligament reconstructive surgery, who have unstable joints because of ligament rupture etc., and thereby have difficulty in sporting activities and daily life.

DESCRIPTION OF EMBODIMENTS

HGF Protein

As described above, "HGF protein" has been identified as a potent mitogen for adult hepatocytes, and is called "Hepatocyte Growth Factor" (see, for example, Non-patent Literatures 4 and 5). In addition to HGF, it is referred to as SF (scatter factor), TCF (Tumor Cytotoxic Factor), etc.

"HGF protein" as used herein is a known substance, and can be prepared by any method as long as it is purified enough to be used as a medicament.

HGF protein can be obtained by culturing primary cultured cells or cell lines capable of producing HGF protein, followed by separation of the HGF protein from culture supernatant etc., and purification. Alternatively, the protein can be obtained by genetic engineering techniques, for example, by inserting the gene encoding HGF protein into an appropriate vector, introducing the vector into an appropriate host cell to be transformed, and isolating a desired recombinant HGF protein from the culture supernatant of the transformant, etc. (see, for example, Japanese Unexamined Patent Publication No. H5-111382, and Biochem. Biophys. Res. Commun., 1989, Vol. 163, p. 967). The above-mentioned host cell is not particularly limited and includes various host cells conventionally used in genetic engineering techniques, for example, *Escherichia coli*, yeast, animal cells, and the like.

In the present invention, a preferable example of HGF protein is a protein obtained from a gene encoding humanderived HGF (hHGF). Preferable examples of the gene encoding hHGF include DNA having the base sequence represented by SEQ ID NO: 1 or 2.

Specific examples of such HGF protein include, according to recombinant DNA techniques, the HGF protein represented by SEQ ID NO: 3 or 5 produced by a cell into which DNA having the base sequence represented by SEQ ID NO: 1 has been introduced, and the HGF protein represented by SEQ ID NO: 4 or 6 produced by a cell into which DNA having the base sequence represented by SEQ ID NO: 2 has been introduced.

The HGF protein represented by SEQ ID NOs. 3 to 6 is a native HGF protein of human origin having mitogen activity and motogen activity as HGF. Such HGF protein is registered, for example, as Accession No. P14210 (SEQ ID NO: 3) or Accession No. NP_001010932 (SEQ ID NO: 4) in the NCBI database (NCBI-GenBank Flat File Release 164.0), or the like. HGF protein having the amino acid sequence represented by SEQ ID NO: 4 is a five amino acid-deleted HGF protein, in which five amino acid residues, i.e., from the $161^{st}$ to the $165^{th}$ residues in the amino acid sequence represented by SEQ ID NO: 3 are deleted. In addition, the aforementioned native HGF protein is glycoprotein. For example, in the HGF protein represented by Accession No. NP_001010932 (SEQ ID NO: 4), a sugar chain is added to Asn 289, Asn 397, Thr 471, Asn 561, and Asn 648.

The amino acid sequence represented by SEQ ID NO: 5 or 6 is an amino acid sequence of an adult protein obtained by cleaving the $1^{st}$ to $31^{st}$ amino acid region (signal sequence) from the N terminus in the amino acid sequence represented by SEQ ID NO: 3 or 4.

As long as the HGF protein used in the present invention has an effect of promoting the regeneration of tendon-bone junction tissue and ligament-bone junction tissue, one or more ("more" means, for example, 2 to 35 amino acids, preferably 2 to 20 amino acids, and more preferably 2 to 10 amino acids; the same shall apply hereinafter) amino acids in the amino acid sequence represented by SEQ ID NO: 3 or 4 may be deleted, substituted, inserted, or added, and similarly, its sugar chain may be deleted, substituted, inserted, or added. Such HGF protein can be produced by known technical methods such as genetic engineering techniques, site specific mutagenesis, etc. An amino acid to be inserted, substituted, or added may be an unnatural amino acid other than 20 kinds of natural amino acids. The unnatural amino acid may be any compound as long as it has an amino group and a carboxyl group, and for example, γ-amino butyric acid etc., is included. In addition, the HGF protein having the amino acid sequence represented by SEQ ID NO: 4 is, as described above, a five amino acid-deleted type HGF protein, in which five amino acid residues in the amino acid sequence represented by SEQ ID NO: 3 are deleted.

The HGF protein used in the present invention may have an amino acid sequence at least 85% homologous to the amino acid sequence represented by SEQ ID NO: 3 or 4 provided that the protein has an effect of promoting the regeneration of tendon-bone junction tissue or ligament-bone junction tissue. HGF protein having an amino acid sequence at least 90% homologous to the amino acid sequence represented by SEQ ID NO: 3 or 4 is preferred, and HGF protein having an amino acid sequence at least 95% homologous to the amino acid sequence represented by SEQ ID NO: 3 or 4 is more preferred. The amino acid sequence represented by SEQ ID NO: 5 is 95.7% and 96.4% homologous to the amino acid sequence represented by SEQ ID NO: 3 and 4, respectively; and the amino acid sequence represented by SEQ ID NO: 6 is 95.1% and 95.7% homologous to the amino acid sequence represented by SEQ ID NO: 3 and 4, respectively. Herein, "homologous to" indicates the degree of identity between the amino acid residues that form each of the sequences when the primary structures (amino acid sequences) of the proteins are compared.

Other examples of HGF protein having an amino acid sequence that is highly homologous to the amino acid sequence represented by SEQ ID NO: 3 or 4 include humanderived HGF registered as Accession No. BAA14348 or AAC71655 in the NCBI database.

As long as the HGF protein used in the present invention has an effect of promoting the regeneration of tendon-bone junction tissue or ligament-bone junction tissue, the signal sequence comprising the $1^{st}$ to $31^{st}$ amino acid region in the amino acid sequence represented by SEQ ID NO: 3 or 4 may be replaced with a signal sequence of another protein. Examples of the signal sequence include a signal sequence of human serum albumin, interferon, human amylase, etc.

As long as the HGF protein used in the present invention has an effect of promoting the regeneration of tendon-bone junction tissue or ligament-bone junction tissue, it may be a protein produced by a cell having DNA that hybridizes with DNA comprising a base sequence complementary to the base sequence represented by SEQ ID NO: 1 or 2 under a stringent condition.

The stringent condition is as follows.

Hybridization is carried out at about 65° C. in the presence of about 0.7 to 1.0 M sodium chloride, and then washing is conducted at about 65° C. in SSC solution at about a 0.1- to 2-fold concentration (a one fold concentration of SSC solution consists of 150 mM sodium chloride and 15 mM sodium citrate).

An example of a method for producing the HGF protein of the present invention using a cell that comprises a gene coding the HGF protein, for example DNA having the base sequence represented by SEQ ID NO: 1 or 2, or DNA that hybridizes with DNA having a base sequence complementary to the aforementioned DNA under a stringent condition is a method in which primary cultured cells or cell lines having the aforementioned DNA are cultured, followed by separation of a desired HGF protein from the culture supernatant etc., and purification. Alternatively, the protein can be obtained by genetic engineering techniques, for example, by inserting the aforementioned DNA into an appropriate vector, introducing the vector into an appropriate host cell to be transformed, and isolating a desired HGF protein (recombinant protein) from the culture supernatant of the transformant (see, for example, Japanese Unexamined Patent Publication No. H5-111382, Japanese Unexamined Patent Publication No. H11-1499, and Biochem. Biophys. Res. Commun., 1989, Vol. 163, p. 967).

The aforementioned host cell is not particularly limited and various host cells conventionally used in genetic engineering techniques, for example, *Escherichia coli*, yeast, animal cells, and the like can be used. Since native HGF protein is a glycoprotein, it is preferred to use an animal cell as a host cell to produce glycoprotein as in the case of using a cell.

Examples of the animal cell include CHO cells, COS cells, mouse L cells, mouse C127 cells, mouse FM3A2 cells, and the like. The expression vector is introduced into an animal cell by transfection methods, microinjection methods, etc. Of these, the most commonly used method is a phosphoric-acid calcium method. For the animal cell that is transformed by transfection, floating cultivation, or adhesion cultivation can be used in accordance with an ordinary method. As a medium, MEM, RPMI 1640, and the like are commonly used.

Whether the HGF protein has an effect of promoting the regeneration of tendon-bone junction tissue or ligament-bone junction tissue can be evaluated as follows.

For example, at least a bone and a tendon or ligament separated from the bone are kept immobilized using a ligament fastener etc. The target HGF protein is then reacted according to the method described in the Example below. Compared to the case where nothing is reacted (control), if effective regeneration of tendon-bone junction tissue or ligament-bone junction tissue is observed when the HGF protein is reacted, the HGF protein is considered to have an effect of promoting the regeneration of tendon-bone junction tissue or ligament-bone junction tissue.

The presence or absence of glycosylation, and the number of glycosylation sites are not particularly limited as long as the HGF protein used in the present invention has an effect of promoting the regeneration of tendon-bone junction tissue or ligament-bone junction tissue.

Specifically, the HGF protein may be protein in which naturally occurring sugar chains (one or more) are deleted, substituted, inserted or added. Examples of the HGF protein in which a sugar chain is deleted, substituted, inserted, or added include HGF protein in which a sugar chain attached to native HGF protein has been deleted by treatment with an enzyme or the like, HGF protein in which the amino acid sequence at the glycosylation site has been mutated so as to prevent glycosylation, or HGF protein in which the amino acid sequence has been mutated so that glycosylation occurs at any other site than the naturally-occurring glycosylation site. Specific examples of such HGF protein include HGF protein that is designed to prevent glycosylation by replacing Asn289, Asn397, Thr471, Asn561, and Asn648 with Gln289, Gln397, Gly471, Gln561, and Gln648, respectively in human HGF protein registered as Accession No. NP_001010932 in the NCBI database (NCBI-GenBank Flat File Release 164.0) (Fukuta, K. et al., Biochemical Journal, 2005, Vol. 388, pp. 555-562).

The HGF protein used in the present invention has any one of a carboxyl group (—COOH), a carboxylate (—COOM (M represents a metal)), an amide (—CONH$_2$), or an ester (—COOR) in the C-terminus. Herein, R in the ester may be a $C_{1-6}$ alkyl group such as methyl, ethyl, n-propyl, isopropyl, and n-butyl; a $C_{3-8}$ cycloalkyl group such as cyclopentyl and cyclohexyl; a $C_{6-12}$ aryl group such as phenyl and α-naphthyl; a $C_{7-14}$ aralkyl group such as a phenyl-($C_{1-2}$ alkyl) group including benzyl and phenethyl, and an α-naphthyl-($C_{1-2}$ alkyl) group including α-naphthylmethyl; a $C_{2-6}$ alkanoylmethyl group such as acetyloxymethyl and pivaloyloxymethyl; etc.

When the HGF protein used in the present invention has a carboxyl group or a carboxylate in any other site than the C-terminus, the carboxyl group or carboxylate may be amidated or esterified. Such HGF protein is also included in the HGF protein used in the present invention. In this case, examples of the ester include the above-mentioned examples of the ester in the C-terminus.

The HGF protein used in the present invention includes the above-mentioned protein having an amino group of the N-terminal methionine residue protected with a protecting group (for example, a $C_{1-6}$ acyl group including a formyl group and a $C_{2-6}$ alkanoyl group such as acetyl, etc.), the above-mentioned protein having a glutamyl group pyroglutamated after being produced by cleaving the N-terminal side in vivo, the above-mentioned protein having a side chain reactive group of the amino acid in a molecule (for example, —OH, —SH, an amino group, an imidazolyl group, an indolyl group, a guanidino group, etc.) protected with an appropriate protecting group (for example, a $C_{1-6}$ acyl group including a formyl group and a $C_{2-6}$ alkanoyl group (e.g., acetyl), etc.), and a complex protein such as a glycoprotein, which is produced by glycosylating the above-mentioned protein.

As the HGF protein used in the present invention, the above-mentioned protein of human origin is suitably used for human application. In addition, HGF protein derived from mammals other than humans, such as monkeys, cattle, horses, pigs, sheep, dogs, cats, rats, mice, rabbits, hamsters, guinea pigs, and chimpanzees, may be used.

Such HGF protein includes, but is not limited to, HGF protein registered in the NCBI database, for example, mouse HGF protein (for example, registered as Accession No. AAB31855, NP_034557, BAA01065, BAA01064, or the like), rat HGF protein (for example, registered as Accession No. NP_058713, bovine HGF protein (for example, registered as Accession No. NP_001026921, BAD02475, or the like), feline HGF protein (for example, registered as Accession No. NP_001009830, BAC10545, BAB21499, or the like), canine HGF protein (for example, registered as Accession No. NP_001002964, BAC57560, or the like), chimpanzee HGF protein (for example, registered as Accession No. XP 519174 or the like), etc.

When the HGF protein is used as the active ingredient of the promoter of the present invention, the HGF protein can be produced by any methods as long as it is purified enough to be used as a medicament. The purification methods are not limited, and examples thereof include column chromatography using heparin sepharose, hydroxyapatite, etc.

In the promoter of the present invention, HGF protein may be used alone, or as a mixed protein with various proteins as long as the effect of promoting the regeneration of tendon-bone junction tissue or ligament-bone junction tissue is not impaired.

HGF Partial Peptide Having Effect of Promoting Regeneration of Tendon-Bone Junction Tissue or Ligament-Bone Junction Tissue The partial peptide of HGF protein used in the present invention (sometimes hereinafter abbreviated as HGF partial peptide), the peptide having an effect of promoting the regeneration of tendon-bone junction tissue or ligament-bone junction tissue is not limited as long as it is a partial peptide of the aforementioned HGF protein and has an effect of promoting the regeneration of tendon-bone junction tissue or ligament-bone junction tissue as in the aforementioned HGF protein. In the present invention, the HGF partial peptide has an amino acid sequence that constitutes the above-mentioned HGF protein and comprises about 20 amino acids or more, preferably about 50 amino acids or more, and more preferably about 100 amino acids or more. Specifically, examples of such an HGF partial peptide include a peptide having an amino acid sequence between the $32^{nd}$ and the $210^{th}$ residues from the N-terminus in the human HGF amino acid sequence represented by SEQ ID NO: 3 (an amino acid sequence from the N-terminal hairpin loop to the $1^{st}$ kringle domain of HGF), a peptide having the amino acid sequence between the $32^{nd}$ and the $288^{th}$ residues from the N-terminus in the human HGF amino acid sequence represented by SEQ ID NO: 3 (an amino acid sequence from the N-terminal hairpin loop to the $2^{nd}$ kringle domain of HGF), and the like.

Examples of the HGF partial peptide of the present invention include a partial peptide having an amino acid sequence at least about 80%, preferably at least about 90%, and more preferably at least about 95% homologous to the amino acid sequence of the aforementioned HGF partial peptide, and having an effect of promoting the regeneration of tendon-bone junction tissue or ligament-bone junction tissue.

The HGF partial peptide of the present invention has any one of a carboxyl group (—COOH), a carboxylate (—COOM (M is the same as defined above)), an amide (—CONH$_2$), or an ester (—COOR(R is the same as defined above)) in the C-terminus. Further, as in the above-mentioned HGF protein, the HGF partial peptide includes a peptide having an amino group of the N-terminal methionine residue protected with a protecting group, a peptide having a glutamyl group pyroglutamated after being produced by cleaving the N-terminal side in vivo, a peptide having a side chain substituent group of the amino acid within a molecule protected with an appropriate protecting group, and a complex protein such as a glycoprotein, which is produced by glycosylating the above-mentioned peptide.

Regarding the HGF partial peptide, "an effect of promoting the regeneration of tendon-bone junction tissue or ligament-bone junction tissue" can be evaluated in the same manner as described above.

The HGF partial peptide of the present invention can be prepared by known peptide synthesis methods or by cleaving HGF protein with an appropriate peptidase. A peptide synthesis method may be, for example, a solid- or liquid-phase synthesis method. Namely, the desired peptide can be prepared by condensing a partial peptide or an amino acid that is capable of constituting HGF protein and optionally having a protecting group with a remaining part optionally having a protecting group; and then by removing the protecting group, if any, from the product. Known condensation or protecting group removal methods include those described in, for example, M. Bodanszky and M. A. Ondetti, Peptide Synthesis, Interscience Publishers, New York (1966); Schroeder and Luebke, The Peptide, Academic Press, New York (1965); etc. After the reaction, HGF partial peptide can be separated and purified by a combination of ordinal purification methods such as solvent extraction, distillation, column chromatography, liquid chromatography, crystallization, or recrystallization.

Salt of HGF Protein or Partial Peptide

The HGF protein or its partial peptide of the present invention may be in a free form (loose body), or the form of a salt.

Examples of the salt of HGF protein or its partial peptide used in the present invention include salts that are physiologically acceptable with an acid or base. Particularly, physiologically acceptable acid adduct salts are preferred. Examples of such salts include salts with inorganic acid (such as hydrochloric acid, phosphoric acid, hydrobromic acid, sulfuric acid, and the like) and salts with organic acid (such as acetic acid, formic acid, propionic acid, fumaric acid, maleic acid, succinic acid, tartaric acid, citric acid, malic acid, oxalic acid, benzoic acid, methanesulfonic acid, benzenesulfonic acid, and the like).

In the production, when the HGF protein or the HGF partial peptide of the present invention is used in a free form, it can be converted into an appropriate salt by a known method. Meanwhile, when the HGF protein or HGF partial peptide is obtained in the form of a salt, it can be converted into a free form by a known method.

DNA Encoding HGF Protein

Herein, "DNA encoding HGF protein" refers to DNA capable of expressing the HGF protein. Preferable examples of DNA that contains DNA encoding HGF protein include DNA encoding human-derived HGF protein described in, for example, Nature, Vol. 342, p. 440 (1989); Japanese Patent No. 2777678; Biochem. Biophys. Res. Commun., 1989, Vol. 163, pp. 967-973; and Proc. Natl. Acad. Sci. U.S.A., 1991, Vol. 88 (16), pp. 7001-7005, and registered as Accession No. M69718, M73240, AC004960, AY246560, M29145, M73240, or the like in GenBank/EMBL/DDBJ.

As DNA encoding HGF protein used in the present invention, the above-mentioned DNA of human origin is suitably used for human application. In addition, DNA encoding HGF protein derived from mammals other than humans, such as monkeys, cattle, horses, pigs, sheep, dogs, cats, rats, mice, rabbits, hamsters, guinea pigs, and chimpanzees may be used.

Such DNA encoding HGF protein includes, but is not limited to, those registered in the NCBI database, for example, DNA encoding mouse HGF protein (for example, registered as Accession Nos. 571816, NM_010427, D10213, D10212, or the like), DNA encoding rat HGF protein (for example, registered as Accession No. NM_017017 or the like), DNA encoding bovine HGF protein (for example, registered as Accession Nos. NM_001031751, AB110822, or the like), DNA encoding feline HGF protein (for example, registered as Accession Nos. NM_001009830, AB080187, AB046610, or the like), DNA encoding canine HGF protein (for example, registered as Accession Nos. NM_001002964, AB090353, or the like), and DNA encoding chimpanzee HGF protein (for example, registered as Accession No. XM 519174 or the like).

Specific examples of DNA encoding HGF protein include DNA having the base sequence represented by SEQ ID NO: 1 or 2. The base sequence represented by SEQ ID NO: 1 corresponds to the region from the $73^{rd}$ to the $2259^{th}$ of the base sequence registered as Accession No. M60718, and also corresponds to DNA encoding HGF protein having the amino acid sequence represented by SEQ ID NO: 3. In recombinant DNA techniques, the HGF protein (SEQ ID NO: 3) that is expressed and produced in a cell is converted into adult HGF protein having the amino acid sequence represented by SEQ ID NO: 5 because the signal sequence is cleaved when the HGF protein is secreted outside the cell. Accordingly, DNA having the base sequence represented by SEQ ID NO: 1 corresponds to DNA encoding (producing) HGF protein having the amino acid sequence represented by SEQ ID NO: 5.

The base sequence represented by SEQ ID NO: 2 corresponds to the region from the $66^{th}$ to the $2237^{th}$ of the base sequence registered as Accession No. M73240, and corresponds to DNA encoding HGF protein comprising the amino acid sequence represented by SEQ ID NO: 4. Similarly, in recombinant DNA techniques, the HGF protein (SEQ ID NO: 4) is converted into adult HGF protein having the amino acid sequence represented by SEQ ID NO: 6 because the signal sequence is cleaved when the HGF protein is secreted outside the cell. Accordingly, DNA having the base sequence represented by SEQ ID NO: 2 corresponds to DNA encoding (producing) HGF protein having the amino acid sequence represented by SEQ ID NO: 6.

DNA encoding HGF protein is not limited to the aforementioned DNA, and any DNA encoding protein having an effect of promoting the regeneration of tendon-bone junction tissue or ligament-bone junction tissue can be used as the DNA encoding HGF protein of the present invention. Herein, "the effect of promoting the regeneration of tendon-bone junction tissue or ligament-bone junction tissue" can be evaluated in the same manner as described above.

Such DNA is not particularly limited, but examples include DNA that has a base sequence at least about 80%, preferably at least about 85%, more preferably at least about 90%, and even more preferably at least about 95% homologous to the base sequence of the aforementioned DNA encoding HGF protein, and encodes a protein having an effect of promoting the regeneration of tendon-bone junction tissue or ligament-bone junction tissue.

The DNA encoding HGF protein can be easily obtained by a general hybridization method or PCR method using a cDNA library containing the DNA. Specifically, the DNA can be obtained with reference to Molecular Cloning, A laboratory Manual, Third Edition (J. Sambrook et al., Cold Spring Harbor Lab. Press, 2001; hereinafter abbreviated as Third Edition Molecular Cloning) and other basic manuals.

Examples of the cDNA library comprising HGF protein-encoding DNA include a human liver cDNA library, a human spleen cDNA library, a human placentas cDNA library, and the like. These libraries can be commercially available from Clonetech, Co., Ltd. or the like. Other than the above, cDNA libraries produced in compliance with a known method by cell strains or tissue materials that express HGF protein can be used. According to the method described in "Third Edition Molecular Cloning", a λ phage in which such cDNA has been incorporated infects *Escherichia coli* for culture. The plaque formed is then subjected to plaque hybridization or PCR using, as a probe, an oligonucleotide that is produced by a base sequence based on the partial amino acid sequence of HGF protein, thereby yielding a desired DNA encoding HGF protein.

In the present invention, RNA encoding HGF protein can also be used as long as the HGF protein can be expressed by reverse transcriptase. Examples of the RNA include RNA obtained by RT-PCR amplification of mRNA fractions harvested from cells or tissues, which is within the scope of the present invention. The RNA also can be obtained by known methods.

As described below, the DNA encoding HGF protein is administered to a patient in the form of a recombinant expression vector in which DNA is inserted. Examples of the expression vector include, but are not limited to, naked plasmids, and DNA or RNA viruses such as detoxified retroviruses, adenoviruses, adeno-associated viruses, herpes viruses (herpes simplex virus type 1, etc.), vaccinia viruses, poxviruses, polioviruses, sindbis viruses, Sendai viruses, SV40, and human immunodeficiency viruses (HIV). Of these, herpes simplex virus type 1 (HSV-1) vectors, Sendai virus envelope (HVJ-E) vectors, adenovirus vectors, adeno-associated virus (AAV) vectors, etc., are preferred.

DNA Encoding Protein Having Effect of Promoting Regeneration of Tendon-Bone Junction Tissue or Ligament-Bone Junction Tissue, and Hybridizing with DNA Comprising Base Sequence Complementary to DNA Encoding HGF Protein Under Stringent Condition The promoter for the regeneration of tendon-bone junction tissue or ligament-bone junction tissue of the present invention may contain DNA coding protein that has an effect of promoting the regeneration of tendon-bone junction tissue or ligament-bone junction tissue as in the HGF protein, and hybridizing with DNA comprising a base sequence complementary to the DNA encoding HGF protein under a stringent condition.

Preferred examples of such DNA include DNA coding protein that has an effect of promoting the regeneration of tendon-bone junction tissue or ligament-bone junction tissue, and hybridizing with DNA comprising a base sequence complementary to the DNA having the base sequence represented by SEQ ID NO: 1 or 2 under a stringent condition.

Herein, "effect of promoting the regeneration of tendon-bone junction tissue or ligament-bone junction tissue" can be evaluated in the same manner as described above.

"The DNA that hybridizes under a stringent condition with DNA comprising a base sequence complementary to the DNA encoding HGF protein, or with DNA comprising a base sequence complementary to the DNA having the base sequence represented by SEQ ID NO: 1 or 2" indicates DNA obtained by using a partial sequence of DNA comprising a base sequence complementary to the DNA encoding HGF protein, or with DNA comprising a base sequence complementary to the DNA having the base sequence represented by SEQ ID NO: 1 or 2 as a probe, and then carrying out colony hybridization, plaque hybridization, or southern blot hybridization. Specifically, DNA identified by the following procedures is included. A filter on which colony- or plaque-derived DNA has been immobilized is subjected to, using the probe, hybridization at about 65° C. in the presence of about 0.7 to 1.0M sodium chloride, and then the filter is washed at about 65° C. in SSC solution at about 0.1- to 2-fold concentration (a one fold concentration of SSC solution consists of 150 mM sodium chloride and 15 mM sodium citrate). The stringent condition will be the same hereinafter.

Specifically, DNA that hybridizes under such a stringent condition includes DNA having a base sequence at least about 80%, preferably at least about 85%, more preferably at least about 90%, and even more preferably at least about 95% homologous to the base sequence of the aforementioned DNA encoding HGF protein. More specifically, DNA that hybridizes with DNA comprising a base sequence complementary to the DNA having the base sequence represented by SEQ ID NO: 1 or 2 under a stringent condition includes DNA having a base sequence at least about 80%, preferably at least about 85%, more preferably at least about 90%, and even more preferably at least about 95% homologous to the base sequence represented by SEQ ID NO: 1 or 2.

Hybridization can be performed according to known methods, for example the method described in Molecular Cloning, Third Edition. When a commercially available library is used, hybridization also can be performed in compliance with the method described in the attached instruction manual.

DNA Encoding HGF Partial Peptide Having Effect of Promoting Regeneration of Tendon-Bone Junction Tissue or Ligament-Bone Junction Tissue The promoter for the regeneration of tendon-bone junction tissue or ligament-bone junction tissue of the present invention may include DNA encoding HGF partial peptide that has an effect of promoting the regeneration of tendon-bone junction tissue or ligament-bone junction tissue. Herein, "effect of promoting the regeneration of tendon-bone junction tissue or ligament-bone junction tissue" can be evaluated in the same manner as described above.

The DNA is not limited as long as it encodes a peptide that has a base sequence encoding the partial peptide and has an effect of promoting the regeneration of tendon-bone junction tissue or ligament-bone junction tissue. Specifically, examples of the DNA include DNA that has a partial base sequence of DNA having the base sequence represented by SEQ ID NO: 1 or 2, and encodes a peptide having an effect of promoting the regeneration of tendon-bone junction tissue or ligament-bone junction tissue as in the HGF protein.

Preferred examples of the DNA include DNA having the region from the $94^{th}$ to the $630^{th}$ of the human HGF base sequence represented by SEQ ID NO: 1 (DNA encoding a peptide from the N-terminal hairpin loop to the $1^{st}$ kringle domain of HGF protein), and DNA having the region from the $94^{th}$ to the $864^{th}$ of the human HGF base sequence represented by SEQ ID NO: 1 (DNA encoding a peptide from the N-terminal hairpin loop to the $2^{nd}$ kringle domain of HGF).

Such DNA is not particularly limited to those described above, and includes DNA encoding a peptide that has an effect of promoting the regeneration of tendon-bone junction tissue or ligament-bone junction tissue, and has a base sequence at least about 80%, preferably at least about 85%, more preferably at least about 90%, and even more preferably at least about 95% homologous to the base sequence of the DNA encoding HGF partial peptide having an effect of promoting the regeneration of tendon-bone junction tissue or ligament-bone junction tissue.

The DNA can be easily obtained by, for example, a general hybridization or PCR method. Specifically, the DNA can be obtained with reference to basic manuals, for example, the above-mentioned Third Edition Molecular Cloning and the like.

Examples of DNA that contains DNA encoding HGF partial peptide having an effect of promoting the regeneration of tendon-bone junction tissue or ligament-bone junction tissue preferably include genomic DNA, genomic DNA library, cell- or tissue-derived cDNA, cell- or tissue-derived cDNA library, synthetic DNA, and the like. Examples of vectors used for the cloning of genomic DNA fragments into the above-mentioned library include bacteriophages, plasmids, cosmids, phagemids, and the like.

In the present invention, any RNA encoding HGF partial peptide having an effect of promoting the regeneration of tendon-bone junction tissue or ligament-bone junction tissue can be used as long as HGF protein can be expressed by reverse transcriptase. Examples of the RNA include RNA obtained by RT-PCR amplification of mRNA fractions harvested from cells or tissues, which is within the scope of the present invention. The RNA also can be obtained by known methods.

DNA that Encodes Peptide Having Effect of Promoting Regeneration of Tendon-Bone Junction Tissue or Ligament-Bone Junction Tissue, and that Hybridizes Under Stringent Condition with DNA Comprising Complementary Base Sequence of DNA Encoding HGF Partial Peptide Having Effect of Promoting Regeneration of Tendon-Bone Junction Tissue or Ligament-Bone Junction Tissue The promoter for the regeneration of tendon-bone junction tissue or ligament-bone junction tissue of the present invention may contain DNA that encodes a peptide having an effect of promoting the regeneration of tendon-bone junction tissue or ligament-bone junction tissue, and that hybridizes under a stringent condition with DNA comprising a base sequence complementary to the DNA encoding HGF partial peptide having an effect of promoting the regeneration of tendon-bone junction tissue or ligament-bone junction tissue.

Such DNA includes DNA that has a base sequence at least about 80%, preferably at least about 85%, more preferably at least about 90%, and even more preferably at least about 95% homologous to the base sequence of the aforementioned DNA encoding HGF partial peptide, and encodes a peptide having an effect of promoting the regeneration of tendon-bone junction tissue or ligament-bone junction tissue.

Examples of such DNA include DNA that encodes a peptide having an effect of promoting the regeneration of tendon-bone junction tissue or ligament-bone junction tissue, and hybridizes under a stringent condition with DNA comprising a base sequence complementary to DNA having a partial base sequence of DNA comprising the base sequence represented by SEQ ID NO: 1 or 2.

Specific examples of such DNA include DNA that has a base sequence at least about 80%, preferably at least about 85%, more preferably at least about 90%, and even more preferably at least about 95% homologous to the base sequence of DNA encoding a partial peptide of DNA having the base sequence represented by SEQ ID NO: 1 or 2, and encodes a peptide having an effect of promoting the regeneration of tendon-bone junction tissue or ligament-bone junction tissue.

Herein, "effect of promoting the regeneration of tendon-bone junction tissue or ligament-bone junction tissue" can be evaluated in the same manner as described above. In addition, hybridization under a stringent condition is the same as defined above.

Regeneration of Tendon-Bone Junction Tissue or Ligament-Bone Junction Tissue

"Tendon" can usually be defined as tissue that connects skeletal muscles to bones, and "ligament" can usually be defined as tissue that connects bones to bones. In the present invention, however, "tendon" may include the meaning of a ligament that connects bones to bones. The tendon used in the present invention may include a graft of tendon (hereinafter sometimes referred to as a "tendon graft"), and the ligament used in the present invention may include a graft of ligament (hereinafter sometimes referred to as a "ligament graft").

Tendon grafts may be Lendon autografts or allografts. Typically, tendon autografts to be used may be taken from hamstrings, patellar tendons, or femoral flexor tendons. Tendon allografts generally used are extracted from cadavers, particularly from their hamstrings, patellar tendons, femoral flexor tendons, Achilles tendons, tendons of tibiae or elbows, etc. Synthetic (or artificial) tendon grafts or tendon xenografts may be used. Tendon grafts in which a tendon autograft (or tendon allograft) is hybridized with a synthetic tendon graft etc., may be used. The tendon graft may be multiply folded for use.

Ligament grafts may be ligament autografts or allograft. Typically, ligament autografts to be used may be extracted from iliotibial tracts etc. Ligament allografts generally used are extracted from cadavers, particularly from their iliotibial tracts, medial collateral ligaments (MCLs), lateral collateral ligaments (LCLs), anterior cruciate ligaments (ACLS), posterior cruciate ligaments (PCLs), outside ligaments, triangular ligaments, tibiofibular ligaments, coracoclavicular ligaments, ligaments of the heads of femora, and the like. Synthetic (or artificial) ligament grafts or ligament xenografts may be used. Ligament grafts in which a ligament autograft (or allograft) is hybridized with a synthetic ligament graft may be used. The ligament graft may be multiply folded for use.

The "tendon-bone junction" and "ligament-bone junction" are not particularly limited as long as they refer to a region in which a tendon or a ligament is adhered to (fixated or fused with) a bone. Examples thereof include a region where a tendon graft is adhered to the inner surface of a bone tunnel (hole) that is made for securing the tendon graft in ligament reconstructive surgery. The bone tunnel is drilled using, for example, a drill guide, drill, etc.

Examples of ligament reconstructive surgery include ligament reconstructive surgery of the knee joint, ankle joint, elbow joint, wrist joint, shoulder joint, and the like. Specific examples thereof include ACL, PCL, or collateral ligament reconstructive surgery of the knee joint, MPFL reconstructive surgery for recurrent patellar dislocation, lateral ankle ligament reconstructive surgery, ulnar elbow ligament reconstructive surgery, surgery for repairing the rotator cuff of the shoulder joint, and the like.

For example, in ACL reconstructive surgery using a tendon graft, a bone tunnel is established at the upper end (proximal end) of the tibia and the lower end of the femur. After the bone tunnel is drilled, the tendon graft is passed through the bone tunnel and secured so that the graft runs between the tibia and the femur while having substantially the same function as the original ACL. Since the tendon-bone junction tissue is reconstructed at a site where the immobilized tendon graft is in contact with the inner surface of the bone tunnel, or in a space between the tendon graft and the bone tunnel, the tendon graft can serve as a ligament, allowing the recovery of the normal function of the knee joint. Thereby, a ligament is reconstructed between the tibia and the femur.

Immobilization can be performed using a bone screw (interference fit screw) or a similar fastener, a ligament fastener, suture (for example, nylon thread, silk thread, etc.), etc. A fastener, ligament fastener, and suture can be used alone or in combination. Examples of the ligament fastener include a stainless steel washer (produced by Zimmer K. K.), Endo Button (produced by Smith and Nephew Endoscopy Co., Ltd.), etc.

The tendon-bone junction or the ligament-bone junction has complicated anatomic features; for example, they include a collagen fiber layer that contains Sharpey-like fibers.

It is also possible to express "regeneration" as "reconstruction". "Regeneration" indicates that tendon-bone junction tissue or ligament-bone junction tissue is reconstructed. For example, in ligament reconstructive surgery, "regeneration" includes any condition in which the grafted tendon (or grafted ligament) having sufficient strength is adhered to (fixated or fused with) a bone, and physiologically functions in vivo.

Regeneration of the tendon-bone junction tissue or the ligament-bone junction tissue includes the following steps (1) to (5):

(1) a step in which non-directional granulation tissues are formed between the bone and the tendon or ligament graft;
(2) a step in which collagen fibers are formed between the bone and the tendon or the ligament graft;
(3) a step in which the collagen fibers are oriented toward the bone;
(4) a step in which Sharpey-like fibers that enter into bone tissue emerge from the tendon or ligament graft; and
(5) a step in which the Sharpey-like fibers mature.

The same applies to regeneration in surgeries other than ligament reconstructive surgery.

Promoter for Regeneration of Tendon-Bone Junction Tissue or Ligament-Bone Junction Tissue Depending on the type of active ingredient, the promoter for regenerating tendon-bone junction tissue or ligament-bone junction tissue of the present invention can be classified into (a) a promoter comprising HGF protein/partial peptide as an active ingredient, and (b) a promoter comprising a HGF gene as an active ingredient.

(a) Promoter Comprising HGF Protein/Partial Peptide as Active Ingredient

A promoter that comprises as an active ingredient, HGF protein as explained in Item (2) above, partial peptide of HGF protein (HGF partial peptide) as explained in Item (3) above, or a salt of at least one of the HGF protein or partial peptide (hereinbelow sometimes referred to as "HGF protein/partial peptide").

(b) Promoter Comprising HGF Gene as Active Ingredient

A promoter comprising as an active ingredient, DNA encoding HGF protein as explained in Item (4) above, (5) DNA hybridizing with the DNA under a stringent condition, DNA encoding HGF partial peptide as explained in Item (6) above, (7) DNA hybridizing with the DNA under a stringent condition (hereinafter, each refereed to as "HGF gene").

In administering the promoter for regeneration of tendon-bone junction tissue or ligament-bone junction tissue of the present invention to a patient, the dosage form, dosing method, dose, etc., may vary when the aforementioned "HGF protein/partial peptide" is used as an active ingredient or the aforementioned "HGF gene" is used as an active ingredient.

The dosage form, dosing method, dose, etc., of the promoter of the present invention can be suitably designed or modified depending on the type of active ingredient.

(a) Promoter Containing HGF Protein/Partial Peptide as Active Ingredient

The promoter (a) can be in any of various dosage forms such as a liquid or solid form. In general, it is preferred that HGF protein, HGF partial peptide, or a salt thereof is formulated in combination with a known carrier into an injection, spray, sustained-release formulation (for example, depot formulation), or the like. The injection or spray may be an aqueous or oily formulation.

The aqueous injection can be prepared by known methods. For example, an aqueous solvent such as water for injection and purified water, is optionally added a pharmaceutically acceptable additive, such as a tonicity agent (e.g., sodium chloride, potassium chloride, glycerin, mannitol, sorbitol, boric acid, borax, glucose, and propylene glycol), a buffer solution (e.g., phosphate buffer solution, acetate buffer solution, borate buffer solution, carbonate buffer solution, citrate buffer solution, Tris-buffer solution, glutamic acid buffer solution, and epsilon-aminocaproic acid buffer solution), a preservative (e.g., methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, sodium edetate, boric acid, and borax), a thickener (e.g., hydroxyethyl cellulose, hydroxypropyl cellulose, polyvinyl alcohol, and polyethylene glycol), a stabilizer (e.g., sucrose, sodium bisulfite, sodium thiosulfate, sodium edetate, sodium citrate, ascorbic acid, and dibutyl hydroxytoluene), a pH adjuster (e.g., hydrochloric acid, sodium hydroxide, phosphoric acid, and acetic acid) or the like. After HGF protein is dissolved, the solution is sterile-filtered with a filter or the like. The filtered solution is then filled into a sterile container.

Additionally, an appropriate solubilizing agent, such as an alcohol (e.g., ethanol), polyalcohol (e.g., propylene glycol, and polyethylene glycol), a nonionic surfactant (e.g., polysorbate 80 and polyoxyethylene 50 hydrogenated castor oil) or the like may also be added. To prepare an oily injection, sesame oil, soy bean oil, or the like may be used as an oily solvent, and benzyl benzoate, benzyl alcohol, or the like may be added as a solubilizing agent. The prepared injection is usually filled into an appropriate ampoule, vial, etc. The amount of the HGF protein in the injection is not limited, but usually can be adjusted to about 0.0002 to 0.5 w/v %, preferably about 0.001 to 0.2 w/v %, based on the total amount of the injection. A liquid formulation such as an injection is preferably freeze-stored, or stored after removing moisture by lyophilization or the like. The lyophilized formulation can be used by adding distilled water for injection or the like as needed and redissolving the formulation.

A spray also can be prepared by common methods in the formulation practice. To prepare a spray, any additive may be added to the spray as long as the additive is usually used for an aerosol. For example, in addition to a propellant, the above-mentioned solvent, preservative, stabilizer, tonicity agent, pH adjuster, etc., can be added. Examples of the propellant include a liquefied gas propellant or a compressed gas. Examples of the liquefied gas propellant include a fluorohydrocarbon (e.g. alternative freon such as HCFC22, HCFC-123, HCFC-134a, dHCFC142, etc.), liquefied petroleum, dimethyl ether, or the like. Examples of the compressed gas include a soluble gas (e.g., carbon dioxide gas and nitrous oxide gas) and an insoluble gas (e.g., nitrogen gas). The amount of the HGF protein in the spray usually can be adjusted to about 0.0002 to 5 w/v %, preferably about 0.001 to 2 w/v %, based on the total amount of the spray.

The HGF protein/partial peptide used in the present invention can be formulated into a sustained-release formulation (e.g., a depot formulation) together with a biodegradable polymer. Specifically, a depot formulation of HGF protein/partial peptide can be expected to reduce dose frequency, prolong effects, and reduce side effects. The sustained-release formulation can be prepared by known methods. The biodegradable polymer to be used in the sustained-release formulation can be appropriately selected from known biodegradable polymers, for example, polysaccharides such as starch, dextran, or chitosan; proteins such as collagen or gelatin; polyamino acids such as polyglutamic acid, polylysine, polyleucine, polyalanine, or polymethionine; polyesters such as polylactic acid, polyglycolic acid, lactic acid-glycolic acid copolymer, polycaprolactone, poly-β-hydroxybutyric acid, polymaleic acid, polyanhydride, or fumaric acid-polyethylene glycol-vinylpyrrolidone copolymer; polyortho esters; polyalkyl cyanoacrylates such as polymethyl-α-cyanoacrylate; polycarbonates such as polyethylene carbonate or polypropylene carbonate. Preferable examples include polyester, polylactic acid, and a lactic acid-glycolic acid copolymer; and more preferable examples include polylactic acid and a lactic acid-glycolic acid copolymer. When a lactic acid-glycolic acid copolymer is used, the composition ratio based on the mole percentage (lactic acid/glycolic acid) varies depending on the duration of sustained release. For example, when the duration of sustained release is from about 2 weeks to 3 months, preferably from about 2 weeks to 1 month, the preferable ratio is from about 100/0 to 50/50. In general, the weight-average molecular weight of the polylactic acid or lactic acid-glycolic acid copolymer is preferably from about 5,000 to 20,000. The polylactic acid or lactic acid-glycolic acid copolymer can be prepared by known methods, for example, the method disclosed in Japanese Unexamined Patent Publication No. S61-28521. The addition ratio of HGF protein and the biodegradable polymer is not particularly limited, but the amount of the HGF protein is generally from about 0.001 to 50 w/w %, and preferably from about 0.01 to 30 w/w %, relative to the biodegradable polymer.

Preferable dosing methods include topical application (direct injection or spray) of an injection or spray to a region (interface) where the bone is in contact with the tendon or ligament graft, or a space between the bone and the tendon or ligament graft, or the surrounding area, and topical application (embedding) of a sustained-release formulation (depot formulation) to the interface or its surrounding area. The dose is appropriately selected according to dosage form, disease progression, age, or the like, and the amount of HGF protein included in the promoter for the regeneration of tendon-bone junction tissue or ligament-bone junction tissue of the present invention is usually 0.1 μg to 500 mg, preferably 1 μg to 50 mg, more preferably 10 μg to 25 mg per dose. In addition, the dose frequency is also appropriately selected according to dosage form, disease progression, age, or the like. A single dosing or continuous dosing at a certain interval can be selected. The continuous dosing may be performed between once daily and once every several months. For example, dosing with the sustained-release formulation (a depot formulation) or continuous dosing with a sustained-release pump may be performed once every several months.

(b) Promoter Containing HGF Gene as Active Ingredient

The HGF gene is delivered to a patient in compliance with conventional methods, for example, the method described in "Idenshi Chiryo No Kiso-gijyutsu (Basic Technique for Gene Therapy)", a separate volume of Experimental Medicine, Yodosha Co., Ltd., 1996; "Idenshi Dounyu & Hatsugen Kaiseki Jikken-hou (Experimental Method for Gene Delivery and Expression Analysis)", a separate volume of Experimental Medicine, Yodosha Co., Ltd., 1997; and "Idenshi Chiryo Kaihatsu Kenkyu Handbook (Handbook for Research & Development in Gene Therapy)" edited by the Japan Society of Gene Therapy, NTS Inc., 1999; etc.

Specific examples thereof include topical application (topical injection) of a recombinant expression vector in which the HGF gene is introduced to the interface or its surrounding tissue (for example, bone, muscle, etc.).

Examples of the expression vector include, but are not limited to, naked plasmids, and DNA or RNA viruses such as detoxified retroviruses, adenoviruses, adeno-associated viruses, herpes viruses (herpes simplex virus type 1, etc.), vaccinia viruses, poxviruses, polioviruses, sindbis viruses, Sendai viruses, SV40, human immunodeficiency viruses (HIV), etc. Of these, preferable examples include herpes simplex virus type 1 (HSV-1) vectors, Sendai virus envelope (HVJ-E) vectors, adenovirus vectors, adeno-associated virus (AAV) vectors, etc.

A specific HSV-1 vector includes a replication-incompetent HSV-1 (HSV1764/4-/pR19) vector that is severely impaired by the deletion of the three respective genes encoding ICR4, ICP34.5 and VP16 (vmw65), all of which are essential for viral replication (see also Coffin, R. S. et al., J. Gen. Virol. 1998, Vol. 79, pp. 3019-3026; Palmer, J. A. et al., J. Virol., 2000, Vol. 74, pp. 5604-5618; Lilley, C. E. et al., J. Virol., 2001, Vol. 75, pp. 4343-4356; etc.). The HVJ-E vector is produced, for example, by the method described in U.S. Pat. No. 6,913,923. For example, as the HVJ-E vector, GenomONE-Neo EX HVJ Envelope Transfection Kit (produced by Cosmo Bio Co., Ltd.) is preferably used. The AAV vector, which is a non-pathogenic virus, is highly safe and efficient in gene delivery into a cell. Examples of the AAV vector include AAV-2, AAV-4, and AAV-5. Such an HSV-1, HVJ-E, or AAV vector is capable of expressing the target gene in a safe manner for a prolonged period of time. An HSV-1, HVJ-E, or AAV vector capable of safe and prolonged expression is most preferable as a vector used in the present invention.

The form of delivering HGF gene into a patient can be selected from various known forms (for example, an injection, spray, sustained-release formulation (depot formulation), microcapsule, etc.) in response to each of the above-mentioned dosing methods. The injection, spray, and sustained-release formulation (depot formulation) can be prepared in the same manner as described in the section HGF protein. The amount of HGF gene delivery vector varies depending on the type of the HGF gene delivery vector and is not limited. For example, when the formulation is in the form of an injection, the amount of gene delivery vector can be generally adjusted to about $1\times10^5$ to $1\times10^{12}$ pfu/mL, and preferably about $1\times10^6$ to $1\times10^{11}$ pfu/mL.

A microcapsule can be prepared as a fine particle with a diameter of about 1 to 500 μm, preferably about 100 to 400 μm, by coating a core substance, for example, a host cell etc., transfected with the HGF gene-containing expression plasmid, with a coating material in accordance with known methods (for example, a coacervation method, interfacial polycondensation, and a method using a double nozzle). Examples of the coating material include a membranous polymer such as carboxymethyl cellulose, cellulose acetate phthalate, ethyl cellulose, alginic acid and a salt thereof, gelatin, gelatin-gum arabic, nitrocellulose, polyvinyl alcohol, hydroxypropyl cellulose, polylactic acid, polyglycolic acid, lactic acid-glycolic acid copolymer, chitosan-alginate, cellulose sulfate-poly(dimethyldiallyl)ammonium chloride, hydroxyethyl methacrylate-methylmethacrylate, chitosan-carboxymethyl cellulose, alginate-polylysine-alginate, and the like.

The amount of HGF gene in the formulation and its dose are appropriately adjusted depending on the type of disease intended to be treated, the age and body weight of the patient, etc. The dose can vary depending on the kind of the HGF gene delivery vector. The HGF gene delivery vector is usually administered in an amount of $1\times10^6$ pfu to $1\times10^{12}$ pfu, preferably $1\times10^7$ pfu to $2\times10^{11}$ pfu, more preferably $1.5\times10^7$ pfu to $1.5\times10^{11}$ pfu once every several days to once every several months.

The promoter of the present invention is suitably applied to humans, as well as other mammals, such as monkeys, cattle, horses, pigs, sheep, dogs, cats, rats, mice, rabbits, hamsters, guinea pigs, chimpanzees, etc.

As described above, the promoter of the present invention is preferably used at a site (interface) where the bone is in contact with the tendon or ligament graft after surgery, or in the surrounding area. The promoter for the regeneration of tendon-bone junction tissue or ligament-bone junction tissue of the present invention can regenerate tendon-bone junction tissue or ligament-bone junction tissue in the interface or the space between the bone and the tendon or ligament graft.

The present invention will be described in more detail below by way of examples; however, the scope of the invention is not limited by these examples.

Example 1

HGF Protein Effect on Regeneration of Tendon-Bone Junction Tissue of Tendon Autograft in Rabbit Model Method: After intramuscular injection of 3 mg of midazolam (Dormicum; produced by Astellas Pharma Inc.) and 1 mg of medetomidine hydrochloride (Domitor: produced by Nippon Zenyaku Kogyo Co., Ltd.), Japanese white rabbits (2.5 to 3.0 kg) were anesthetized by continuous intravenous injection of about 260 mg/h sodium pentobarbital (somnopentyl; produced by Kyoritsu Seiyaku Corporation). Their hind legs were shaved and disinfected, and each leg was subjected to the following surgery under clean condition. First, an approximately 5 cm incision was made on the skin of the anterior aspect of the hind leg. The extension digitorum longus (hereinbelow, abbreviated as EDL) tendon attached to the lateral femoral condyle was cut at the origin (attachment) of the femur. Subsequently, the lateral surface of the tibia was exposed, and a hole (hereinafter referred to as "bone tunnel") was made from the lateral surface to the internal surface of the proximal tibia, using a drill of 2.5 mm in diameter. As shown in FIG. 1, the free end of the EDL tendon (tendon graft) that had been previously cut was pulled into the bone tunnel from the lateral surface of the tibia, then pulled out of the medial surface of the tibia, and secured using a stainless steel washer (produced by Zimmer K.K.) and a 3-0 nylon thread (produced by Bear Medic Corporation). The leg was secured in ankle neutral position. The bone tunnel into which the tendon graft had been pulled was fully washed with physiological saline solution (produced by Otsuka Pharmaceutical Co., Ltd.). Next, cancellous bone containing 10 μL of a mixture obtained by dissolving 10 μg of HGF protein in 10 μL of physiological saline was transplanted to the contact site and space between the bone tunnel and the tendon graft of the right hind leg (HGF administration group). As the HGF protein, HGF protein having the amino acid sequence represented by SEQ ID No. 6 was used. In the contact site and space between the bone tunnel and the tendon graft of the left hind leg, cancellous bone containing 10 μL of physiological saline was transplanted (control group). The cancellous bone collected in the formation of the bone tunnel was used as the cancellous bone (0.05 g). After the transplantation of the cancellous bone, the wound was closed by suture. After the surgery, the rabbits were returned to their cages, and were free to move about without any restriction or immobilization of their extremities.

At 2, 4, 6, 8, and 12 weeks following surgery, nine rabbits each were sacrificed. The tendon graft including the tibia and EDL was taken as a lump of tissue. The distance from the entrance (lateral surface) to the outlet (medial surface) of the hole (bone tunnel) of the proximal tibia was measured using a caliper. Four rabbits were used for histological examination and five rabbits were used for biomechanical testing.

(1) Histological Examination

The extracted tissue was preserved in a 10% (v/v) formalin solution for 2 days, washed with physiological saline, and then immersed in 80% (v/v) methyl alcohol for two days. Subsequently, decalcification was performed using a Plank-Rychlo solution over 7 days. After decalcification, sections were made along the long axis of the bone tunnel of the tibia. The obtained sections were stained with hematoxylin-eosin (HE) and Masson trichrome. The stained sections were observed with an optical microscope and scored using the following criteria.

Score Criteria

−: The formation of new tissue was not observed in the interface (the contact site and the space between the tendon graft and the bone tunnel).

+: The formation of non-directional granulation tissues was observed in the interface.

++: collagen fibers being oriented toward the bone appeared in the interface.

+++: Sharpey-like fibers appeared between collagen fibers oriented toward the bone in the interface.

++++: The Sharpey-like fibers matured into thick fibers.

Results: FIG. 2 shows optical micrographs at 8 weeks after surgery. In comparison with the control group (left figure B), the HGF administration group (right figure A) clearly indicates that Sharpey-like fibers and collagen fibers that were oriented toward the bone appeared in the interface. Additionally, the Sharpey-like fibers matured into thick fibers.

Table 1 shows the interface tissue score. Table 1 clearly indicates that, in the HGF administration group, the formation (regeneration) of tendon-bone junction tissue in the interface was promoted at an early postoperative stage.

TABLE 1

| Group | Score | | | | |
| --- | --- | --- | --- | --- | --- |
| | Two weeks after surgery | Four weeks after surgery | Six weeks after surgery | Eight weeks after surgery | Twelve weeks after surgery |
| Control | + | ++ | +++ | ++++ | ++++ |
| HGF Administration | ++ | +++ | ++++ | ++++ | ++++ |

(2) Biomechanical Testing

Biomechanical testing was carried out by comparing the rupture strength of tendon-bone junction tissue formed when the tendon graft was attached to the bone tunnel. The ultimate load (Newton: N) per millimeter of the length of the bone tunnel, which was obtained when the tendon graft was pulled out of the bone tunnel, was recorded, and the rupture strength was calculated according to the following formula.

Rupture strength (N/mm)=Ultimate load/Bone tunnel length

The ultimate load is obtained as follows. Using a tensile testing machine (4482 model, produced by Instron Co., Ltd.), the tibia of the extracted tissue was secured to the tensile testing machine, and then the EDL was held and pulled along the long axis of the bone tunnel. The load obtained when the tendon graft was pulled out of the bone tunnel was expressed as the ultimate load. Tendon grafts that had ruptured before being pulled out of the bone tunnel were excluded.

Results: Table 2 shows the rupture strength at 2 and 6 weeks after surgery. At both 2 and 6 weeks after surgery, the rupture strength in the HGF administration group was higher than in the control group.

TABLE 2

| Weeks after surgery | Group | Number | Rupture Strength* (N/mm) |
| --- | --- | --- | --- |
| 2 weeks | HGF administration | 5 | 3.59 ± 0.28 |
| | Control | 5 | 2.61 ± 0.91 |
| 4 weeks | HGF administration | 5 | 5.71 ± 0.37 |
| | Control | 4 | 4.24 ± 0.43 |
| 6 weeks | HGF administration | 4 | 6.16 ± 1.17 |
| | Control | 5 | 5.27 ± 1.64 |
| 8 weeks | HGF administration | 4 | 6.72 ± 1.19 |
| | Control | 4 | 5.94 ± 1.25 |
| 12 weeks | HGF administration | 3 | 7.83 ± 1.78 |
| | Control | 4 | 6.50 ± 1.55 |

*Each value indicates average value ± standard deviation

The results reveal that the administration of HGF protein allows for the quick regeneration of strong tendon-bone junction tissue.

Example 2

HGF Protein Effect on Regeneration of Tendon-Bone Junction Tissue of Tendon Autograft in Rabbit Model An experiment was conducted in the same manner as in Example 1 except that the HGF protein having the amino acid sequence represented by SEQ ID NO: 4 was used in place of the HGF protein used above.

The results reveal that the HGF protein had the effect of promoting the regeneration of tendon-bone junction tissue or ligament-bone junction tissue as in Example 1.

Preparation Examples of the promoter of the present invention are described below. In the Preparation Examples, any HGF protein having an amino acid sequence represented by SEQ ID Nos. 3 to 6 can be used as HGF protein.

Preparation Example 1

A solution in which 1 mg of HGF protein, 1 g of mannitol, and 10 mg of polysolvate 80 were added to 100 mL of physiological saline was aseptically prepared. The solution was placed in a vial in an amount of 1 mL, freeze-dried, and sealed to obtain a promoter in the form of a freeze-dried formulation.

Preparation Example 2

An aqueous solution in which 1 mg of HGF protein (SEQ ID No. 6) and 100 mg of human serum albumin were added to 100 mL of 0.02 M phosphate buffer solution was aseptically prepared. The aqueous solution was placed in a vial in an amount of 1 mL, freeze-dried, and sealed to obtain a promoter in the form of a freeze-dried formulation.

Preparation Example 3

1.9 g of lactic acid-glycolic acid copolymer (lactic acid/glycolic acid=50/50, weight average molecular weight=10, 000; produced by Wako Pure Chemical Ind. Ltd.) is dissolved in 3.0 mL of dichloromethane. 100 mg of freeze-dried HGF protein powder is added to the resulting organic solvent mixture, and pulverized using a mixer mill (produced by Retsch) to prepare a HGF dispersion. The dispersion is added to 800 mL of 0.1 w/v % PVA aqueous solution, and the mixture was stirred and emulsified using a homomixer. Dichloromethane is then vaporized by stirring at room temperature for 3 hours, and centrifugation (about 2,000 rpm) is performed to separately collect microcapsules. Subsequently, the microcapsules are washed twice using 400 mL of distilled water, and 0.2 g of D-mannitol is added. The mixture is then freeze-dried. To further remove the solvent residue, the resultant is vacuum-dried at 40° C. for 3 days. Thereby, sustained release microcapsules containing HGF protein are obtained (the addition ratio of HGF to biodegradable polymer: 5.3 w/w %).

Preparation Example 4

1.89 g of lactic acid-glycolic acid copolymer (lactic acid/glycolic acid=50/50, weight average molecular weight=10,000; produced by Wako Pure Chemical Ind. Ltd.) and 10 mg of zinc oxide are dissolved in 3.0 mL of dichloromethane. 100 mg of freeze-dried HGF protein powder is added to the resulting organic solvent mixture, and pulverized using a mixer mill (produced by Retsch) to prepare a HGF dispersion. The dispersion is added to 800 mL of 0.1 w/v % PVA aqueous solution, and the mixture is stirred and emulsified using a homomixer. Dichloromethane is then vaporized by stirring at room temperature for 3 hours, and centrifugation (about 2,000 rpm) is performed to separately collect microcapsules. Subsequently, the microcapsules are washed twice using 400 mL of distilled water, and 0.2 g of D-mannitol is added. The mixture was then freeze-dried. To further remove the solvent residue, the resultant is vacuum-dried at 40° C. for 3 days. Thereby, sustained release microcapsules containing HGF protein are obtained (the addition ratio of HGF to biodegradable polymer: 5.3 w/w %).

Preparation Example 5

1.7 g of lactic acid-glycolic acid copolymer (lactic acid/glycolic acid=75/25, weight average molecular weight=15,000; produced by Wako Pure Chemical Ind. Ltd.) is dissolved in 2.7 mL of dichloromethane. 300 mg of freeze-dried HGF protein powder is added to the resulting organic solvent mixture, and pulverized using a mixer mill (produced by Retsch) to prepare a HGF dispersion. The dispersion is added to 800 mL of 0.1 w/v % PVA aqueous solution, and the mixture is stirred and emulsified using a homomixer. Dichloromethane isvaporized by stirring at room temperature for 3 hours, and centrifugation (about 2,000 rpm) is performed to separately collect microcapsules (about 2,000 rpm). Subsequently, the microcapsules are washed twice using 400 mL of distilled water, and 0.2 g of D-mannitol is added. The mixture is then freeze-dried. To further remove the solvent residue, the resultant is vacuum-dried at 40° C. for 3 days to obtain a sustained release microcapsule containing HGF protein (the addition ratio of HGF to biodegradable polymer: 17.6 w/w %).

Preparation Example 6

1.69 g of lactic acid-glycolic acid copolymer (lactic acid/glycolic acid=75/25, weight average molecular weight=15,000; produced by Wako Pure Chemical Ind. Ltd.) and 10 mg of zinc oxide are dissolved in 2.7 mL of dichloromethane. 300 mg of freeze-dried HGF protein powder is added to the resulting organic solvent mixture, and pulverized using a mixer mill (produced by Retsch) to prepare a HGF dispersion. The dispersion is added to 800 mL of 0.1 w/v % PVA aqueous solution, and the mixture was stirred and emulsified using a homomixer. Dichloromethane is vaporized by stirring at room temperature for 3 hours and centrifugation (about 2,000 rpm) is performed to separately collect microcapsules. Subsequently, the microcapsules are washed twice using 400 mL of distilled water, and 0.2 g of D-mannitol is added. The mixture was then freeze-dried. To further remove the solvent residue, the resultant is vacuum-dried at 40° C. for 3 days to obtain sustained release microcapsules containing HGF protein (the addition ratio of HGF to a biodegradable polymer: 17.8 w/w %).

Preparation Example 7

5 g of DL-lactic acid polymer (lactic acid/glycolic acid=100/0, weight average molecular weight=5,000; produced by Wako Pure Chemical Ind. Ltd.) is dissolved in 50 mL of methylene chloride to obtain a 10 w/v % solution. Subsequently, 2.5 mg of freeze-dried HGF protein powder is added to the mixture. The resulting mixture is added to a 0.5 w/v % chitosan aqueous solution that had been separately heated to 40° C., and stirred and emulsified by a homomixer at a stirring rate of 1000 rpm. The emulsion obtained is further stirred for 3 hours at room temperature to evaporate methylene chloride. Subsequently, microspheres obtained by centrifuging (about 2,000 rpm) are collected and washed five times with distilled water that had been heated to 40° C. Subsequently, drying under reduced pressure is carried out at room temperature, and microspheres containing HGF are obtained (the addition ratio of HGF to biodegradable polymer: 0.05 w/w %).

Preparation Example 8

10 g of lactic acid-glycolic acid copolymer (lactic acid/glycolic acid=75/25, weight average molecular weight=5,000; produced by Wako Pure Chemical Ind. Ltd.) is dissolved in 200 mL of a mixture containing methylene chloride and ethanol (4:1) to prepare a 5 w/v % solution. Subsequently, 2.5 mg of freeze-dried HGF protein powder is added to the solution. The mixture is then gradually added to a 1 w/v % gelatin aqueous solution that had been separately heated to 40° C. while stirring at a rate of 500 rpm using a homomixer, and emulsified. The emulsion obtained is further stirred for 3 hours at room temperature to evaporate methylene chloride and ethanol. Subsequently, microspheres obtained by centrifuging (about 2,000 rpm) are collected. The collected microspheres are washed five times with distilled water that had been heated to 40° C., and dried under reduced pressure at room temperature to obtain microspheres containing HGF protein (the addition ratio of HGF to biodegradable polymer: 0.025 w/w %).

Preparation Example 9

0.2 mL of 2 w/v % HGF-containing aqueous solution and 2 mL of 2 w/v % atelocollagen-containing phosphate buffer solution are mixed and freeze-dried. The HGF-containing aqueous solution can be prepared by the method according to Preparation Example 1. The resulting freeze-dried product is pulverized under low temperature using liquid nitrogen, and then subjected to molding compression using a mold to obtain a cylindrical sustained release formulation containing HGF protein (the addition ratio of HGF to a biodegradable polymer: 10 w/w %).

Preparation Example 10

100 mL of 0.01 w/v % HGF-containing aqueous solution and 50 g of 2 w/v % collagen aqueous solution are uniformly mixed while stirring, and freeze-dried. Thereafter, low temperature pulverization is carried out using liquid nitrogen. The resultant is subjected to compression molding to form a rod shape. The sustained release formulation containing HGF protein (addition ratio of HGF to biodegradable polymer: 1 w/w %) was thus obtained.

Preparation Example 11

1 mg of HGF protein is dissolved in 2 mL of 2 w/v % atelocollagen solution, and the mixture is freeze-dried. The resulting freeze-dried product is pulverized, and then subjected to compression molding to form a cylindrical shape. The sustained release formulation containing HGF protein is thus obtained (the addition ratio of HGF to biodegradable polymer: 2.5 mass %).

Preparation Example 12

0.58 g of sodium salt of hyaluronan (limiting viscosity number: 45,000 cc/g) and 20 mL of water are mixed and allowed to swell. 2 mL of 2N sodium hydrate is added to the mixture, and stirred to form a homogeneous solution. A solution prepared by adding 0.10 g of divinyl sulfone to 2.4 mL of water while stirring is added to the aforementioned solution to form a mixture. The mixture is allowed to stand for 70 min to obtain a gel. The gel is introduced into 223 mL of BioTris buffer solution (0.15M NaCl phosphate buffer, pH: about 7.2) and allowed to swell for 3 hours. Subsequently, 1 mL of 2N HCl is added to the swollen gel. One hour later, 0.6 mL of 2N HCl is added thereto and allowed to stand for 16 hours. Then, 0.35 mL of 2N HCl is added, and the swollen gel was stirred slowly in the buffer solution for three days to obtain a soft gel with homogeneous viscoelasticity. The gel is dialyzed against 0.15M NaCl for five days. The gel is mixed with 1 w/v % HGF in buffered saline, and the final concentration of HGF protein is set at 0.25 w/v %. The formulation containing HGF is thus obtained (the addition ratio of HGF to biodegradable polymer: about 25 w/v %).

INDUSTRIAL APPLICABILITY

The promoter for the regeneration of a tendon- or ligament-bone junction tissue of the present invention is useful as a medical drug for promoting the regeneration of a tendon- or ligament-bone junction tissue.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 2A shows the HE-staining image of the HGF administration group and FIG. 2B shows the HE-staining image of the control group.

EXPLANATION OF NUMERALS

Figure 1:
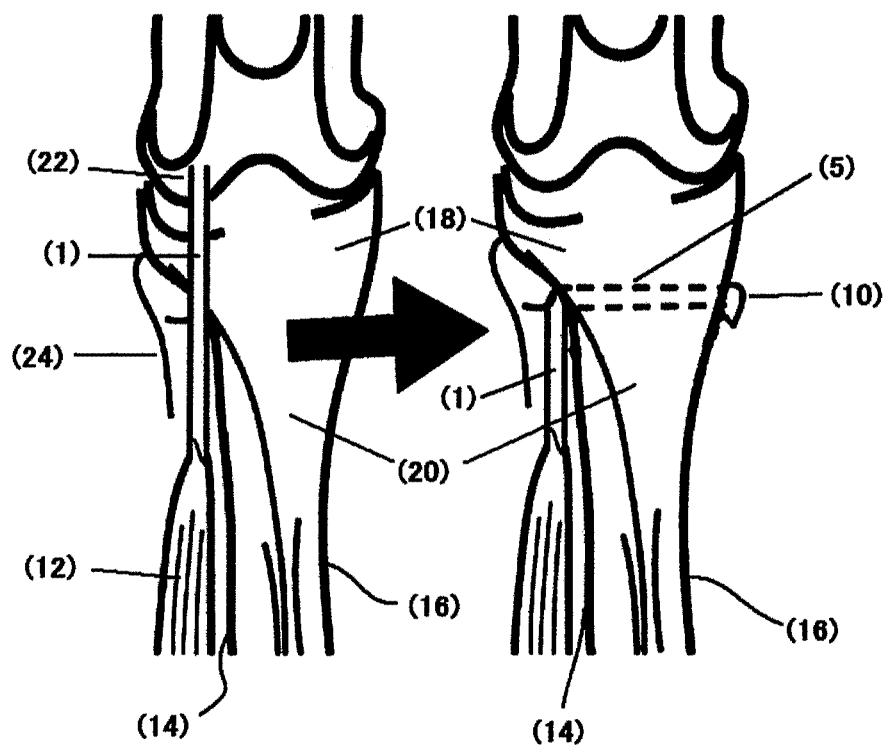
FIG. 1 shows the EDL tendon of the rabbit ankle joint in Example 1 (left figure), and an embodiment in which the EDL tendon has been transplanted into the bone (right figure).
Figure 2:
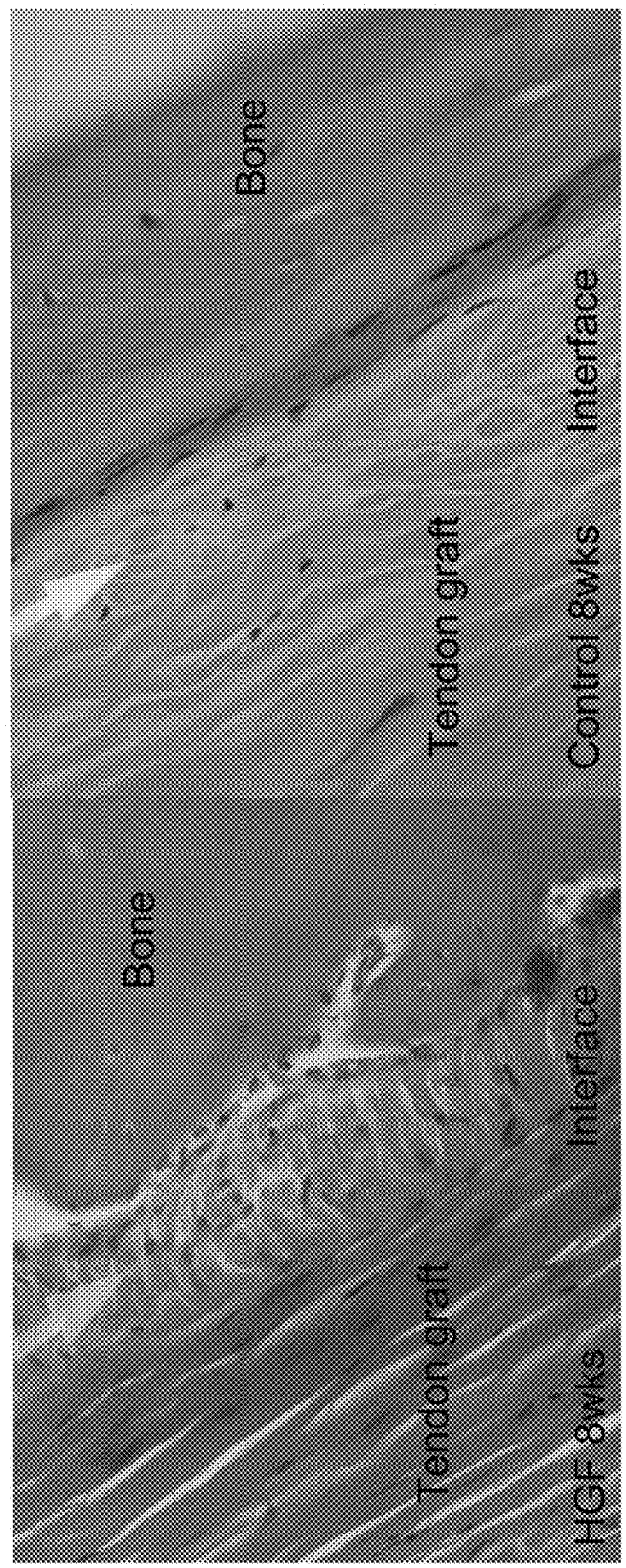
FIG. 2 shows the optical microscope photographs of the tendon-bone junction tissue at 8 weeks following EDL tendon transplantation in Example 1. Specifically.

1. Extension digitorum longus tendon (EDL tendon)
5. Bone tunnel
10. Stainless steel washer
12. Extension digitorum longus (EDL)
14. Lateral surface of tibia
16. Medial surface of tibia
18. Proximal tibia
20. Tibia
22. Lateral femoral condyle
24. Fibula

The invention claimed is:

1. A method for promoting regeneration of tendon-bone junction tissue or ligament-bone junction tissue consisting essentially of administering the following (1) or (2) to a patient with tendon-bone junction tissue injury or ligament-bone junction tissue injury:
   (1) a Hepatocyte Growth Factor (HGF) protein having an amino acid sequence at least 95% homologous to the amino acid sequence represented by SEQ ID NO: 3, and having an effect of promoting regeneration of tendon-bone junction tissue or ligament-bone junction tissue, or
   (2) a formulation consisting of (1), and at least one member selected from the group consisting of aqueous solvent, tonicity agent, buffer solution, preservative, thickener, stabilizer, pH adjuster, solubilizing agent, oily solvent, propellant, and biodegradable polymer,
   wherein (1) or (2) is locally applied to an interface region where the bone is in contact with the tendon or ligament, or a space between the bone and the tendon or ligament.

2. The method according to claim 1, wherein (1) is a protein having the amino acid sequence represented by SEQ ID NO: 3, SEQ ID NO: 4, SEQ ID NO: 5, or SEQ ID NO: 6.

3. The method according to claim 1, wherein the patient has had surgery to repair the injury, in which a graft of tendon is adhered to the bone or a graft of ligament is adhered to the bone.

4. The method according to claim 3, wherein the surgery is ligament reconstruction surgery where a tendon graft is adhered to an inner surface of a bone tunnel that is made for securing the tendon graft or where a ligament graft is adhered to an inner surface of a bone tunnel that is made for securing the ligament graft.

5. The method according to claim 4, wherein the ligament reconstructive surgery is anterior cruciate ligament (ACL) reconstructive surgery, posterior cruciate ligament (PCL) reconstructive surgery, or collateral ligament reconstructive surgery, for a knee joint; MPFL reconstructive surgery for recurrent patellar dislocation; lateral ankle ligament reconstructive surgery; or surgery for repairing a rotator cuff of a shoulder joint.

* * * * *

SEQUENCE LISTING

```
<160> NUMBER OF SEQ ID NOS: 6

<210> SEQ ID NO 1
<211> LENGTH: 2187
<212> TYPE: DNA
<213> ORGANISM: Homo sapiens

<400> SEQUENCE: 1
atgtgggtga ccaaactcct gccagccctg ctgctgcagc atgtcctcct gcatctcctc      60
ctgctcccca tcgccatccc ctatgcagag ggacaaagga aagaagaaa tacaattcat     120 gaattcaaaa aatcagcaaa gactacccta atcaaaatag atccagcact gaagataaaa     180
accaaaaaag tgaatactgc agaccaatgt gctaatagat gtactaggaa taaaggactt     240
ccattcactt gcaaggcttt tgtttttgat aaagcaagaa aacaatgcct ctggttcccc     300
ttcaatagca tgtcaagtgg agtgaaaaaa gaatttggcc atgaatttga cctctatgaa     360
aacaaagact acattagaaa ctgcatcatt ggtaaaggac gcagctacaa gggaacagta     420
tctatcacta agagtggcat caaatgtcag ccctggagtt ccatgatacc acacgaacac     480 agcttttgc cttcgagcta tcggggtaaa gacctacagg aaaactactg tcgaaatcct     540
```

| | |
|---|---|
| cgaggggaag aaggggggacc ctggtgtttc acaagcaatc cagaggtacg ctacgaagtc | 600 |
| tgtgacattc ctcagtgttc agaagttgaa tgcatgacct gcaatgggga gagttatcga | 660 |
| ggtctcatgg atcatacaga atcaggcaag atttgtcagc gctgggatca tcagacacca | 720 |
| caccggcaca aattcttgcc tgaaagatat cccgacaagg gctttgatga taattattgc | 780 |
| cgcaatcccg atggccagcc gaggccatgg tgctatactc ttgaccctca cacccgctgg | 840 |
| gagtactgtg caattaaaac atgcgctgac aatactatga atgacactga tgttcctttg | 900 |
| gaaacaactg aatgcatcca aggtcaagga gaaggctaca ggggcactgt caataccatt | 960 |
| tggaatggaa ttccatgtca gcgttgggat tctcagtatc ctcacgagca tgacatgact | 1020 |
| cctgaaaatt tcaagtgcaa ggacctacga gaaaattact gccgaaatcc agatgggtct | 1080 |
| gaatcaccct ggtgttttac cactgatcca aacatccgag ttggctactg ctcccaaatt | 1140 |
| ccaaactgtg atatgtcaca tggacaagat tgttatcgtg ggaatggcaa aaattatatg | 1200 |
| ggcaacttat cccaaacaag atctggacta acatgttcaa tgtgggacaa gaacatggaa | 1260 |
| gacttacatc gtcatatctt ctgggaacca gatgcaagta agctgaatga gaattactgc | 1320 |
| cgaaatccag atgatgatgc tcatggaccc tggtgctaca cgggaaatcc actcattcct | 1380 |
| tgggattatt gccctatttc tcgttgtgaa ggtgatacca cacctacaat agtcaattta | 1440 |
| gaccatcccg taatatcttg tgccaaaacg aaacaattgc gagttgtaaa tgggattcca | 1500 |
| acacgaacaa acataggatg gatggttagt ttgagataca gaaataaaca tatctgcgga | 1560 |
| ggatcattga taaaggagag ttgggttctt actgcacgac agtgtttccc ttctcgagac | 1620 |
| ttgaaagatt atgaagcttg gcttggaatt catgatgtcc acggaagagg agatgagaaa | 1680 |
| tgcaaacagg ttctcaatgt ttcccagctg gtatatggcc ctgaaggatc agatctggtt | 1740 |
| ttaatgaagc ttgccaggcc tgctgtcctg gatgattttg ttagtacgat tgatttaccct | 1800 |
| aattatggat gcacaattcc tgaaaagacc agttgcagtg tttatggctg ggcctacact | 1860 |
| ggattgatca actatgatgg cctattacga gtggcacatc tctatataat gggaaatgag | 1920 |
| aaatgcagcc agcatcatcg agggaaggtg actctgaatg agtctgaaat atgtgctggg | 1980 |
| gctgaaaaga ttggatcagg accatgtgag ggggattatg gtggcccact tgtttgtgag | 2040 |
| caacataaaa tgagaatggt tcttggtgtc attgttcctg gtcgtggatg tgccattcca | 2100 |
| aatcgtcctg gtattttgt ccgagtagca tattatgcaa atggatacac caaaattatt | 2160 |
| ttaacatata aggtaccaca gtcatag | 2187 |

<210> SEQ ID NO 2
<211> LENGTH: 2172
<212> TYPE: DNA
<213> ORGANISM: Homo sapiens

<400> SEQUENCE: 2

| | |
|---|---|
| atgtgggtga ccaaactcct gccagccctg ctgctgcagc atgtcctcct gcatctcctc | 60 |
| ctgctcccca tcgccatccc ctatgcagag ggacaaagga aagaagaaa tacaattcat | 120 |
| gaattcaaaa aatcagcaaa gactacccta atcaaaatag atccagcact gaagataaaa | 180 |
| accaaaaaag tgaatactgc agaccaatgt gctaatagat gtactaggaa taaggacttt | 240 |
| ccattcactt gcaaggcttt tgtttttgat aaagcaagaa acaatgcct ctggttcccc | 300 |
| ttcaatagca tgtcaagtgg agtgaaaaaa gaatttggcc atgaatttga cctctatgaa | 360 |
| aacaaagact acattagaaa ctgcatcatt ggtaaaggac gcagctacaa gggaacagta | 420 |

| | |
|---|---|
| tctatcacta agagtggcat caaatgtcag ccctggagtt ccatgatacc acacgaacac | 480 |
| agctatcggg gtaaagacct acaggaaaac tactgtcgaa atcctcgagg ggaagaaggg | 540 |
| ggaccctggt gtttcacaag caatccagag gtacgctacg aagtctgtga cattcctcag | 600 |
| tgttcagaag ttgaatgcat gacctgcaat ggggagagtt atcgaggtct catggatcat | 660 |
| acagaatcag gcaagatttg tcagcgctgg gatcatcaga caccacaccg gcacaaattc | 720 |
| ttgcctgaaa gatatcccga caagggcttt gatgataatt attgccgcaa tcccgatggc | 780 |
| cagccgaggc catggtgcta tactcttgac cctcacaccc gctgggagta ctgtgcaatt | 840 |
| aaaacatgcg ctgacaatac tatgaatgac actgatgttc ctttggaaac aactgaatgc | 900 |
| atccaaggtc aaggagaagg ctacaggggc actgtcaata ccatttggaa tggaattcca | 960 |
| tgtcagcgtt gggattctca gtatcctcac gagcatgaca tgactcctga aaatttcaag | 1020 |
| tgcaaggacc tacgagaaaa ttactgccga aatccagatg ggtctgaatc accctggtgt | 1080 |
| tttaccactg atccaaacat ccgagttggc tactgctccc aaattccaaa ctgtgatatg | 1140 |
| tcacatggac aagattgtta tcgtgggaat ggcaaaaatt atatgggcaa cttatcccaa | 1200 |
| acaagatctg gactaacatg ttcaatgtgg gacaagaaca tggaagactt acatcgtcat | 1260 |
| atcttctggg aaccagatgc aagtaagctg aatgagaatt actgccgaaa tccagatgat | 1320 |
| gatgctcatg gaccctggtg ctacacggga atccactca ttccttggga ttattgccct | 1380 |
| atttctcgtt gtgaaggtga taccacacct acaatagtca atttagacca tcccgtaata | 1440 |
| tcttgtgcca aaacgaaaca attgcgagtt gtaaatggga ttccaacacg aacaaacata | 1500 |
| ggatggatgg ttagtttgag atacagaaat aaacatatct gcggaggatc attgataaag | 1560 |
| gagagttggg ttcttactgc acgacagtgt ttcccttctc gagacttgaa agattatgaa | 1620 |
| gcttggcttg gaattcatga tgtccacgga agaggagatg agaaatgcaa acaggttctc | 1680 |
| aatgtttccc agctggtata tggccctgaa ggatcagatc tggttttaat gaagcttgcc | 1740 |
| aggcctgctg tcctggatga ttttgttagt acgattgatt tacctaatta tggatgcaca | 1800 |
| attcctgaaa agaccagttg cagtgtttat ggctggggct acactggatt gatcaactat | 1860 |
| gatggcctat tacgagtggc acatctctat ataatgggaa atgagaaatg cagccagcat | 1920 |
| catcgaggga aggtgactct gaatgagtct gaaatatgtg ctggggctga aaagattgga | 1980 |
| tcaggaccat gtgaggggga ttatggtggc ccacttgttt gtgagcaaca taaaatgaga | 2040 |
| atggttcttg gtgtcattgt tcctggtcgt ggatgtgcca ttccaaatcg tcctggtatt | 2100 |
| tttgtccgag tagcatatta tgcaaaatgg atacacaaaa ttattttaac atataaggta | 2160 |
| ccacagtcat ag | 2172 |

<210> SEQ ID NO 3
<211> LENGTH: 728
<212> TYPE: PRT
<213> ORGANISM: Homo sapiens

<400> SEQUENCE: 3

Met Trp Val Thr Lys Leu Leu Pro Ala Leu Leu Leu Gln His Val Leu
1               5                   10                  15

Leu His Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

-continued

```
Asn Thr Ala Asp Gln Cys Ala Asn Arg Cys Thr Arg Asn Lys Gly Leu
 65                  70                  75                  80

Pro Phe Thr Cys Lys Ala Phe Val Phe Asp Lys Ala Arg Lys Gln Cys
                 85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
            115                 120                 125

Ile Ile Gly Lys Gly Arg Ser Tyr Lys Gly Thr Val Ser Ile Thr Lys
        130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
            195                 200                 205

Val Glu Cys Met Thr Cys Asn Gly Glu Ser Tyr Arg Gly Leu Met Asp
210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
            275                 280                 285

Ala Asp Asn Thr Met Asn Asp Thr Asp Val Pro Leu Glu Thr Thr Glu
290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
            355                 360                 365

Asp Pro Asn Ile Arg Val Gly Tyr Cys Ser Gln Ile Pro Asn Cys Asp
            370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
            435                 440                 445

Gly Pro Trp Cys Tyr Thr Gly Asn Pro Leu Ile Pro Trp Asp Tyr Cys
            450                 455                 460

Pro Ile Ser Arg Cys Glu Gly Asp Thr Thr Pro Thr Ile Val Asn Leu
465                 470                 475                 480
```

```
Asp His Pro Val Ile Ser Cys Ala Lys Thr Lys Gln Leu Arg Val Val
            485                 490                 495

Asn Gly Ile Pro Thr Arg Thr Asn Ile Gly Trp Met Val Ser Leu Arg
        500                 505                 510

Tyr Arg Asn Lys His Ile Cys Gly Gly Ser Leu Ile Lys Glu Ser Trp
    515                 520                 525

Val Leu Thr Ala Arg Gln Cys Phe Pro Ser Arg Asp Leu Lys Asp Tyr
530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 4
<211> LENGTH: 723
<212> TYPE: PRT
<213> ORGANISM: Homo sapiens

<400> SEQUENCE: 4

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125
```

-continued

```
Ile Ile Gly Lys Gly Arg Ser Tyr Lys Gly Thr Val Ser Ile Thr Lys
130                 135                 140
Ser Gly Ile Lys Cys Gln Pro Trp Ser Ser Met Ile Pro His Glu His
145                 150                 155                 160
Ser Tyr Arg Gly Lys Asp Leu Gln Glu Asn Tyr Cys Arg Asn Pro Arg
                165                 170                 175
Gly Glu Glu Gly Gly Pro Trp Cys Phe Thr Ser Asn Pro Glu Val Arg
                180                 185                 190
Tyr Glu Val Cys Asp Ile Pro Gln Cys Ser Glu Val Glu Cys Met Thr
        195                 200                 205
Cys Asn Gly Glu Ser Tyr Arg Gly Leu Met Asp His Thr Glu Ser Gly
210                 215                 220
Lys Ile Cys Gln Arg Trp Asp His Gln Thr Pro His Arg His Lys Phe
225                 230                 235                 240
Leu Pro Glu Arg Tyr Pro Asp Lys Gly Phe Asp Asp Asn Tyr Cys Arg
                245                 250                 255
Asn Pro Asp Gly Gln Pro Arg Pro Trp Cys Tyr Thr Leu Asp Pro His
                260                 265                 270
Thr Arg Trp Glu Tyr Cys Ala Ile Lys Thr Cys Ala Asp Asn Thr Met
            275                 280                 285
Asn Asp Thr Asp Val Pro Leu Glu Thr Thr Glu Cys Ile Gln Gly Gln
290                 295                 300
Gly Glu Gly Tyr Arg Gly Thr Val Asn Thr Ile Trp Asn Gly Ile Pro
305                 310                 315                 320
Cys Gln Arg Trp Asp Ser Gln Tyr Pro His Glu His Asp Met Thr Pro
                325                 330                 335
Glu Asn Phe Lys Cys Lys Asp Leu Arg Glu Asn Tyr Cys Arg Asn Pro
                340                 345                 350
Asp Gly Ser Glu Ser Pro Trp Cys Phe Thr Thr Asp Pro Asn Ile Arg
                355                 360                 365
Val Gly Tyr Cys Ser Gln Ile Pro Asn Cys Asp Met Ser His Gly Gln
370                 375                 380
Asp Cys Tyr Arg Gly Asn Gly Lys Asn Tyr Met Gly Asn Leu Ser Gln
385                 390                 395                 400
Thr Arg Ser Gly Leu Thr Cys Ser Met Trp Asp Lys Asn Met Glu Asp
                405                 410                 415
Leu His Arg His Ile Phe Trp Glu Pro Asp Ala Ser Lys Leu Asn Glu
                420                 425                 430
Asn Tyr Cys Arg Asn Pro Asp Asp Ala His Gly Pro Trp Cys Tyr
            435                 440                 445
Thr Gly Asn Pro Leu Ile Pro Trp Asp Tyr Cys Pro Ile Ser Arg Cys
450                 455                 460
Glu Gly Asp Thr Thr Pro Thr Ile Val Asn Leu Asp His Pro Val Ile
465                 470                 475                 480
Ser Cys Ala Lys Thr Lys Gln Leu Arg Val Val Asn Gly Ile Pro Thr
                485                 490                 495
Arg Thr Asn Ile Gly Trp Met Val Ser Leu Arg Tyr Arg Asn Lys His
                500                 505                 510
Ile Cys Gly Gly Ser Leu Ile Lys Glu Ser Trp Val Leu Thr Ala Arg
            515                 520                 525
Gln Cys Phe Pro Ser Arg Asp Leu Lys Asp Tyr Glu Ala Trp Leu Gly
530                 535                 540
```

```
Ile His Asp Val His Gly Arg Gly Asp Glu Lys Cys Lys Gln Val Leu
545                 550                 555                 560

Asn Val Ser Gln Leu Val Tyr Gly Pro Glu Gly Ser Asp Leu Val Leu
            565                 570                 575

Met Lys Leu Ala Arg Pro Ala Val Leu Asp Asp Phe Val Ser Thr Ile
        580                 585                 590

Asp Leu Pro Asn Tyr Gly Cys Thr Ile Pro Glu Lys Thr Ser Cys Ser
    595                 600                 605

Val Tyr Gly Trp Gly Tyr Thr Gly Leu Ile Asn Tyr Asp Gly Leu Leu
610                 615                 620

Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
            645                 650                 655

Glu Lys Ile Gly Ser Gly Pro Cys Glu Gly Asp Tyr Gly Gly Pro Leu
        660                 665                 670

Val Cys Glu Gln His Lys Met Arg Met Val Leu Gly Val Ile Val Pro
    675                 680                 685

Gly Arg Gly Cys Ala Ile Pro Asn Arg Pro Gly Ile Phe Val Arg Val
690                 695                 700

Ala Tyr Tyr Ala Lys Trp Ile His Lys Ile Ile Leu Thr Tyr Lys Val
705                 710                 715                 720

Pro Gln Ser

<210> SEQ ID NO 5
<211> LENGTH: 697
<212> TYPE: PRT
<213> ORGANISM: Homo sapiens

<400> SEQUENCE: 5

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
            20                  25                  30

Val Asn Thr Ala Asp Gln Cys Ala Asn Arg Cys Thr Arg Asn Lys Gly
        35                  40                  45

Leu Pro Phe Thr Cys Lys Ala Phe Val Phe Asp Lys Ala Arg Lys Gln
    50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Phe Leu Pro Ser Ser Tyr Arg Gly Lys Asp Leu Gln Glu Asn
    130                 135                 140

Tyr Cys Arg Asn Pro Arg Gly Glu Glu Gly Gly Pro Trp Cys Phe Thr
145                 150                 155                 160

Ser Asn Pro Glu Val Arg Tyr Glu Val Cys Asp Ile Pro Gln Cys Ser
                165                 170                 175

Glu Val Glu Cys Met Thr Cys Asn Gly Glu Ser Tyr Arg Gly Leu Met
            180                 185                 190
```

```
Asp His Thr Glu Ser Gly Lys Ile Cys Gln Arg Trp Asp His Gln Thr
            195                 200                 205

Pro His Arg His Lys Phe Leu Pro Glu Arg Tyr Pro Asp Lys Gly Phe
        210                 215                 220

Asp Asp Asn Tyr Cys Arg Asn Pro Asp Gly Gln Pro Arg Pro Trp Cys
225                 230                 235                 240

Tyr Thr Leu Asp Pro His Thr Arg Trp Glu Tyr Cys Ala Ile Lys Thr
                245                 250                 255

Cys Ala Asp Asn Thr Met Asn Asp Thr Asp Val Pro Leu Glu Thr Thr
            260                 265                 270

Glu Cys Ile Gln Gly Gln Gly Glu Gly Tyr Arg Gly Thr Val Asn Thr
        275                 280                 285

Ile Trp Asn Gly Ile Pro Cys Gln Arg Trp Asp Ser Gln Tyr Pro His
    290                 295                 300

Glu His Asp Met Thr Pro Glu Asn Phe Lys Cys Lys Asp Leu Arg Glu
305                 310                 315                 320

Asn Tyr Cys Arg Asn Pro Asp Gly Ser Glu Ser Pro Trp Cys Phe Thr
                325                 330                 335

Thr Asp Pro Asn Ile Arg Val Gly Tyr Cys Ser Gln Ile Pro Asn Cys
            340                 345                 350

Asp Met Ser His Gly Gln Asp Cys Tyr Arg Gly Asn Gly Lys Asn Tyr
        355                 360                 365

Met Gly Asn Leu Ser Gln Thr Arg Ser Gly Leu Thr Cys Ser Met Trp
    370                 375                 380

Asp Lys Asn Met Glu Asp Leu His Arg His Ile Phe Trp Glu Pro Asp
385                 390                 395                 400

Ala Ser Lys Leu Asn Glu Asn Tyr Cys Arg Asn Pro Asp Asp Asp Ala
                405                 410                 415

His Gly Pro Trp Cys Tyr Thr Gly Asn Pro Leu Ile Pro Trp Asp Tyr
            420                 425                 430

Cys Pro Ile Ser Arg Cys Glu Gly Asp Thr Thr Pro Thr Ile Val Asn
        435                 440                 445

Leu Asp His Pro Val Ile Ser Cys Ala Lys Thr Lys Gln Leu Arg Val
    450                 455                 460

Val Asn Gly Ile Pro Thr Arg Thr Asn Ile Gly Trp Met Val Ser Leu
465                 470                 475                 480

Arg Tyr Arg Asn Lys His Ile Cys Gly Gly Ser Leu Ile Lys Glu Ser
                485                 490                 495

Trp Val Leu Thr Ala Arg Gln Cys Phe Pro Ser Arg Asp Leu Lys Asp
            500                 505                 510

Tyr Glu Ala Trp Leu Gly Ile His Asp Val His Gly Arg Gly Asp Glu
        515                 520                 525

Lys Cys Lys Gln Val Leu Asn Val Ser Gln Leu Val Tyr Gly Pro Glu
    530                 535                 540

Gly Ser Asp Leu Val Leu Met Lys Leu Ala Arg Pro Ala Val Leu Asp
545                 550                 555                 560

Asp Phe Val Ser Thr Ile Asp Leu Pro Asn Tyr Gly Cys Thr Ile Pro
                565                 570                 575

Glu Lys Thr Ser Cys Ser Val Tyr Gly Trp Gly Tyr Thr Gly Leu Ile
            580                 585                 590

Asn Tyr Asp Gly Leu Leu Arg Val Ala His Leu Tyr Ile Met Gly Asn
        595                 600                 605

Glu Lys Cys Ser Gln His His Arg Gly Lys Val Thr Leu Asn Glu Ser
```

```
            610                 615                 620
Glu Ile Cys Ala Gly Ala Glu Lys Ile Gly Ser Gly Pro Cys Glu Gly
625                 630                 635                 640

Asp Tyr Gly Gly Pro Leu Val Cys Glu Gln His Lys Met Arg Met Val
                    645                 650                 655

Leu Gly Val Ile Val Pro Gly Arg Gly Cys Ala Ile Pro Asn Arg Pro
                660                 665                 670

Gly Ile Phe Val Arg Val Ala Tyr Tyr Ala Lys Trp Ile His Lys Ile
            675                 680                 685

Ile Leu Thr Tyr Lys Val Pro Gln Ser
            690                 695

<210> SEQ ID NO 6
<211> LENGTH: 692
<212> TYPE: PRT
<213> ORGANISM: Homo sapiens

<400> SEQUENCE: 6

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
            20                  25                  30

Val Asn Thr Ala Asp Gln Cys Ala Asn Arg Cys Thr Arg Asn Lys Gly
        35                  40                  45

Leu Pro Phe Thr Cys Lys Ala Phe Val Phe Asp Lys Ala Arg Lys Gln
50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Tyr Arg Gly Lys Asp Leu Gln Glu Asn Tyr Cys Arg Asn Pro
130                 135                 140

Arg Gly Glu Glu Gly Gly Pro Trp Cys Phe Thr Ser Asn Pro Glu Val
145                 150                 155                 160

Arg Tyr Glu Val Cys Asp Ile Pro Gln Cys Ser Glu Val Glu Cys Met
                165                 170                 175

Thr Cys Asn Gly Glu Ser Tyr Arg Gly Leu Met Asp His Thr Glu Ser
            180                 185                 190

Gly Lys Ile Cys Gln Arg Trp Asp His Gln Thr Pro His Arg His Lys
        195                 200                 205

Phe Leu Pro Glu Arg Tyr Pro Asp Lys Gly Phe Asp Asp Asn Tyr Cys
210                 215                 220

Arg Asn Pro Asp Gly Gln Pro Arg Pro Trp Cys Tyr Thr Leu Asp Pro
225                 230                 235                 240

His Thr Arg Trp Glu Tyr Cys Ala Ile Lys Thr Cys Ala Asp Asn Thr
                245                 250                 255

Met Asn Asp Thr Asp Val Pro Leu Glu Thr Thr Glu Cys Ile Gln Gly
            260                 265                 270

Gln Gly Glu Gly Tyr Arg Gly Thr Val Asn Thr Ile Trp Asn Gly Ile
        275                 280                 285
```

```
Pro Cys Gln Arg Trp Asp Ser Gln Tyr Pro His Glu His Asp Met Thr
290                 295                 300
Pro Glu Asn Phe Lys Cys Lys Asp Leu Arg Glu Asn Tyr Cys Arg Asn
305                 310                 315                 320
Pro Asp Gly Ser Glu Ser Pro Trp Cys Phe Thr Thr Asp Pro Asn Ile
            325                 330                 335
Arg Val Gly Tyr Cys Ser Gln Ile Pro Asn Cys Asp Met Ser His Gly
            340                 345                 350
Gln Asp Cys Tyr Arg Gly Asn Gly Lys Asn Tyr Met Gly Asn Leu Ser
        355                 360                 365
Gln Thr Arg Ser Gly Leu Thr Cys Ser Met Trp Asp Lys Asn Met Glu
370                 375                 380
Asp Leu His Arg His Ile Phe Trp Glu Pro Asp Ala Ser Lys Leu Asn
385                 390                 395                 400
Glu Asn Tyr Cys Arg Asn Pro Asp Asp Asp Ala His Gly Pro Trp Cys
            405                 410                 415
Tyr Thr Gly Asn Pro Leu Ile Pro Trp Asp Tyr Cys Pro Ile Ser Arg
            420                 425                 430
Cys Glu Gly Asp Thr Thr Pro Thr Ile Val Asn Leu Asp His Pro Val
        435                 440                 445
Ile Ser Cys Ala Lys Thr Lys Gln Leu Arg Val Val Asn Gly Ile Pro
450                 455                 460
Thr Arg Thr Asn Ile Gly Trp Met Val Ser Leu Arg Tyr Arg Asn Lys
465                 470                 475                 480
His Ile Cys Gly Gly Ser Leu Ile Lys Glu Ser Trp Val Leu Thr Ala
            485                 490                 495
Arg Gln Cys Phe Pro Ser Arg Asp Leu Lys Asp Tyr Glu Ala Trp Leu
            500                 505                 510
Gly Ile His Asp Val His Gly Arg Gly Asp Glu Lys Cys Lys Gln Val
        515                 520                 525
Leu Asn Val Ser Gln Leu Val Tyr Gly Pro Glu Gly Ser Asp Leu Val
530                 535                 540
Leu Met Lys Leu Ala Arg Pro Ala Val Leu Asp Asp Phe Val Ser Thr
545                 550                 555                 560
Ile Asp Leu Pro Asn Tyr Gly Cys Thr Ile Pro Glu Lys Thr Ser Cys
            565                 570                 575
Ser Val Tyr Gly Trp Gly Tyr Thr Gly Leu Ile Asn Tyr Asp Gly Leu
            580                 585                 590
Leu Arg Val Ala His Leu Tyr Ile Met Gly Asn Glu Lys Cys Ser Gln
        595                 600                 605
His His Arg Gly Lys Val Thr Leu Asn Glu Ser Glu Ile Cys Ala Gly
610                 615                 620
Ala Glu Lys Ile Gly Ser Gly Pro Cys Glu Gly Asp Tyr Gly Gly Pro
625                 630                 635                 640
Leu Val Cys Glu Gln His Lys Met Arg Met Val Leu Gly Val Ile Val
            645                 650                 655
Pro Gly Arg Gly Cys Ala Ile Pro Asn Arg Pro Gly Ile Phe Val Arg
            660                 665                 670
Val Ala Tyr Tyr Ala Lys Trp Ile His Lys Ile Ile Leu Thr Tyr Lys
        675                 680                 685
Val Pro Gln Ser
    690
```